United States Patent
Liu et al.

(10) Patent No.: US 12,134,603 B2
(45) Date of Patent: Nov. 5, 2024

(54) SYNTHESIS METHOD FOR N-METHYL-3-SUBSTITUTED METHYL-4-PYRAZOLAMIDE DERIVATIVE AND N-METHYL-3-SUBSTITUTED METHYL-4-PYRAZOLIC ACID

(71) Applicant: Shaoxing Shangyu Xin Yinbang Biochemical Co., Ltd., Zhejiang Province (CN)

(72) Inventors: Shengxue Liu, Zhejiang Province (CN); Yintao Shi, Zhejiang Province (CN); Qiang Gong, Zhejiang Province (CN); Sufang Zhong, Zhejiang Province (CN); Jianjiang Zhang, Zhejiang Province (CN); Xiaoyuan Qian, Zhejiang Province (CN); Fang Guo, Zhejiang Province (CN); Rujun Chen, Zhejiang Province (CN); Xiaoying Jian, Zhejiang Province (CN)

(73) Assignee: Shaoxing Shangyu Xin Yinbang Biochemical Co., Ltd., Zheijiang (CN)

(*) Notice: Subject to any disclaimer, the term of this patent is extended or adjusted under 35 U.S.C. 154(b) by 0 days.

(21) Appl. No.: 18/234,629

(22) Filed: Aug. 16, 2023

(65) Prior Publication Data
US 2024/0083852 A1 Mar. 14, 2024

Related U.S. Application Data

(63) Continuation of application No. PCT/CN2023/088835, filed on Apr. 18, 2023.

(30) Foreign Application Priority Data

Aug. 24, 2022 (CN) .......................... 202211020398.6

(51) Int. Cl.
 C07D 231/14 (2006.01)
 C07D 409/12 (2006.01)
(52) U.S. Cl.
 CPC .......... *C07D 231/14* (2013.01); *C07D 409/12* (2013.01)
(58) Field of Classification Search
 CPC .......................... C07D 231/14; C07D 409/12
 See application file for complete search history.

(56) References Cited

FOREIGN PATENT DOCUMENTS

| CN | 101668524 A | 3/2010 |
| CN | 102066335 A | 5/2011 |
| CN | 103360313 A | 10/2013 |
| CN | 112194642 A | 1/2021 |
| CN | 115141147 A | 10/2022 |
| WO | 2015003289 A1 | 1/2015 |

OTHER PUBLICATIONS

Bohler, et al. DE 2523175 (abstract), Dec. 18, 1975; retrieved from STN, Accession No. 1976:123393.*
Chick, et al. Proceedings of the Chemical Society, London (abstract), 1908; retrieved from STN, Accession No. 1908:9952.*
Dains, et al. Washington Coll. J. Am. Chem. Soc. (abstract), 1910, 31, 1148-57; retrieved from STN; Accession No. 1910:1011.*
Ewins. Proceedings of the Chemical Society, London (abstract), 1913; retrieved from STN, Accession No. 1913:10205.*
Hoechst A. DE 2524959 A1 (abstract), Dec. 9, 1976, retrieved from STN, Accession No. 1977:72626.*
Pyne, et al. Journal of the American Chemical Society (abstract) (1982), 104 (21), 5728-40, retrieved from STN, Accession No. 1982:615848.*
Meyer. Cerichte der Deutschen Chemischen Gesellschaft (abstract) (1906), 39, 198, retrieved from STN, Accession No. 1907:4618.*
International Search Report of Corresponding Application PCT/CN2023/088835, mailed May 22, 2023; 5 pages.
Toth, et al.; Synthesis of 5-(2-chloroalkyl)-2,2-dimethyl-1,3-dioxane-4,6-diones; Synthetic Communications, vol. 32, No. 23, pp. 3659-3365, 2002; 7 Pgs.

* cited by examiner

*Primary Examiner* — Shawquia Jackson
(74) *Attorney, Agent, or Firm* — Cooper Legal Group, LLC

(57) ABSTRACT

The present application relates to a synthesis method for N-methyl-3-substituted methyl-4-pyrazolamide derivative and N-methyl-3-substituted methyl-4-pyrazolic acid, including the following steps: step S1: synthesis of intermediate E; step S2: synthesis of intermediate D; step S3: synthesis of intermediate C; step S4: synthesis of N-methyl-3-substituted methyl-4-pyrazolamide derivative; and synthesis of N-methyl-3-substituted methyl-4-pyrazolic acid by decomposition of N-methyl-3-substituted methyl-4-pyrazolamide derivative.

15 Claims, 15 Drawing Sheets

SYNTHESIS METHOD FOR N-METHYL-3-SUBSTITUTED METHYL-4-PYRAZOLAMIDE DERIVATIVE AND N-METHYL-3-SUBSTITUTED METHYL-4-PYRAZOLIC ACID

CROSS-REFERENCE TO RELATED APPLICATION

This application is a continuation of PCT application serial no. PCT/CN2023/088835, filed on Apr. 18, 2023, which claims the priority and benefit of Chinese patent application serial no. 202211020398.6, filed on Aug. 24, 2022. The entireties of PCT application serial no. PCT/CN2023/088835 and Chinese patent application serial no. 202211020398.6 are hereby incorporated by reference herein and made a part of this specification.

TECHNICAL FIELD

The present application relates to a technical field of organic synthesis, and, in particular, to a synthesis method for N-methyl-3-substituted methyl-4-pyrazolamide derivative and N-methyl-3-substituted methyl-4-pyrazolic acid.

BACKGROUND ART

N-methyl-3-substituted methyl-4-pyrazolamide derivative A generally is prepared through the acylation reaction of N-methyl-3-substituted methyl-4-pyrazolic acid B, and the specific reaction process is as follows:

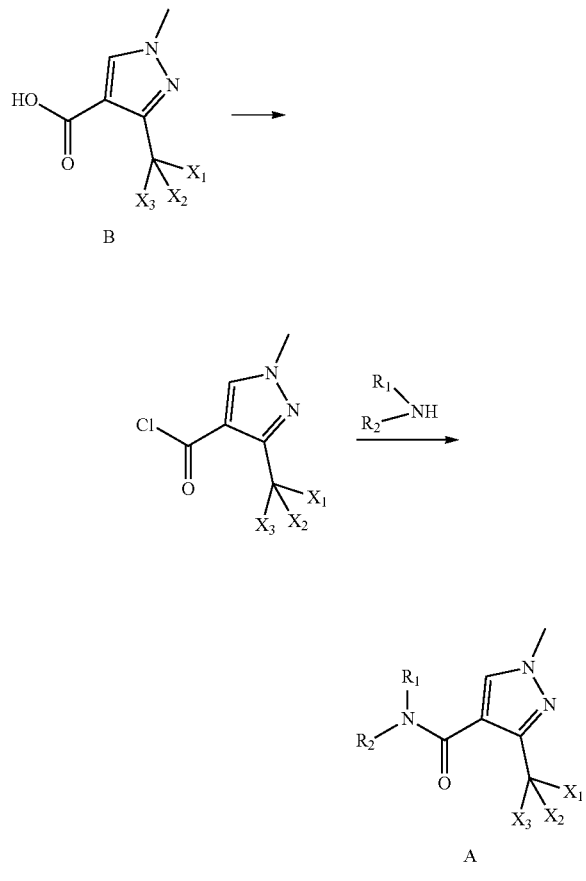

N-methyl-3-substituted methyl-4-pyrazolamide derivative A is widely used in pesticide fungicide and insecticide. As shown in FIG. 1, $X_1$, $X_2$ and $X_3$ in N-methyl-3-substituted methyl-4-pyrazolic acid B are F, F and H respectively, and different N-methyl-3-substituted methyl-4-pyrazolamide derivative $A_{1-9}$ in FIG. 1 can be synthesized. As shown in FIG. 2, when $X_1$, $X_2$ and $X_3$ in N-methyl-3-substituted methyl-4-pyrazolic acid B are F, different N-methyl-3-substituted methyl-4-pyrazolamide derivative $A_{10-12}$ in FIG. 2 can be synthesized. From the above, it can be seen that N-methyl-3-substituted methyl-4-pyrazolic acid B is needed to be synthesized before synthesizing N-methyl-3-substituted methyl-4-pyrazolamide derivative A.

At present, the synthesis routes for N-methyl-3-substituted methyl-4-pyrazolic acid B (mainly difluoro substituted methyl) mainly include 10 routes shown in FIG. 3. In view of the synthesis process, routes 1, 2, 3, 6 and 8 have long synthesis route and low product yield; routes 4 and 5 have the disadvantages of harsh reaction conditions and difficulty in industrial production; routes 9 and 10 have many side reactions, insufficient purity of reaction products, and difficult for controlling reaction conditions; and route 7 has the disadvantages of high raw material price and low product yield. Thus, although there are many mature synthesis routes for N-methyl-3-substituted methyl-4-pyrazolic acid B, there are always some disadvantages in the current synthesis methods.

In view of the disadvantages of the above related technologies, it is believed that it is very necessary to develop the new synthesis routes for N-methyl-3-substituted methyl-4-pyrazolamide derivative A and N-methyl-3-substituted methyl-4-pyrazolic acid B.

SUMMARY

The present application provides the synthesis method for N-methyl-3-substituted methyl-4-pyrazolamide derivative A and N-methyl-3-substituted methyl-4-pyrazolic acid B. In the present application, the synthesis route of N-methyl-3-substituted methyl-4-pyrazolamide derivative is performed by using the new intermediate, which has advantages of cheap and easily available raw materials, short synthesis route and mild reaction condition. In addition, the synthesized N-methyl-3-substituted methyl-4-pyrazolamide derivative can be conversely decomposed to synthesize N-methyl-3-substituted methyl-4-pyrazolic acid, which can further simplify the synthesis steps of N-methyl-3-substituted methyl-4-pyrazolic acid.

In a first aspect, a synthesis method for N-methyl-3-substituted methyl-4-pyrazolamide derivative provided in the present application adopts the following technical solutions:

a synthesis method for N-methyl-3-substituted methyl-4-pyrazolamide derivative includes the following synthesis route:

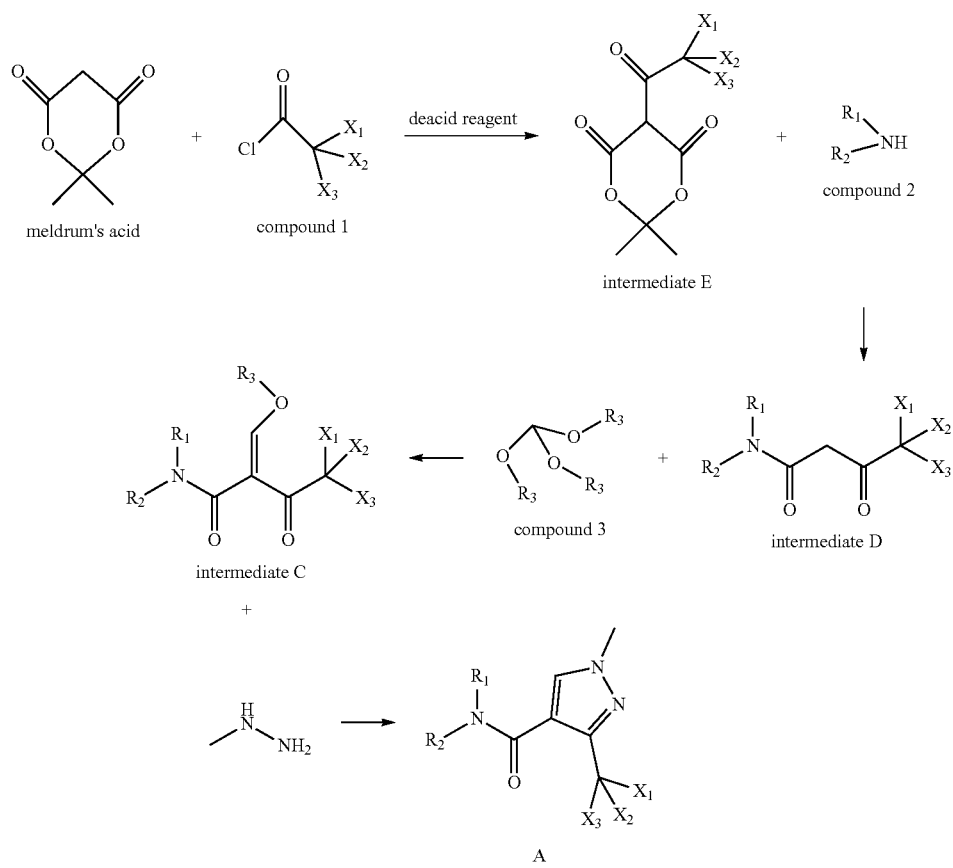

where, X1, X2 and X3 are one selected from a group consisting of H, F, Cl and Br, respectively; R1 and R2 are one selected from a group consisting of H, 1-4 benzene rings or substituted benzene rings, and aliphatic hydrocarbon group or substituted thiophene with 1-8 carbon atoms, respectively.

In some embodiments, step S1 for synthesis of an intermediate E includes: under the protection of nitrogen, adding Meldrum's acid into a solvent, cooling to 0° C. or below, adding an deacid reagent dropwise, stirring, adding Compound 1, holding a temperature, then heating to a reaction temperature for reaction, adding hydrochloric acid into the reaction solution to adjust pH, standing for separation into layers to obtain an organic phase, and subjecting the organic phase to a solvent removing under reduced pressure to obtain the intermediate E.

In some embodiments, step S2 for synthesis of an intermediate D includes: under the protection of nitrogen gas, adding intermediate E obtained in step S1 to a solvent, adding compound 2, performing a heating reflux water separation reaction, then performing solvent removing under reduced pressure to obtain a product, adding a second batch of the solvent to the product, standing at a raised temperature, cooling to 0° C. or below for crystallization, filtering to obtain a filter cake, and drying to obtain the intermediate D.

In some embodiments, step S3 for synthesis of an intermediate C includes: under the protection of nitrogen gas, mixing the intermediate D, an acetic anhydride and Compound 3, heating to a reaction temperature for reaction, cooling, performing reduced pressure distillation, adding ethanol, heating to realize dissolved clarification, cooling to 0° C. or below, then filtering to obtain a filter cake, and drying to obtain the intermediate C; and In some embodiments, step S4 for synthesis of N-methyl-3-substituted methyl-4-pyrazolamide derivative includes: under the protection of nitrogen gas, adding the intermediate C obtained in step S3 to a solvent, maintaining a reaction temperature, adding an aqueous solution of methylhydrazine, maintaining the reaction temperature for reaction, heating to a reflux temperature for further reaction, performing solvent removing under reduced pressure, cooling to 0° C. or below for crystallization, filtering, and drying to obtain N-methyl-3-substituted methyl-4-pyrazolamide derivative A.

In the above technical solutions, the present application designs a new synthesis route, which uses Meldrum's acid as the raw material to obtain N-methyl-3-substituted methyl-4-pyrazolamide derivative A through 4 steps. The synthesis route is short, and thus the yield is higher. Additionally, the synthesis route in the present application avoids the synthesis of N-methyl-3-substituted methyl-4-pyrazolic acid B, and the preparation process is simpler. Moreover, in terms of raw materials, the raw materials in the present application are cheap and easily available, which can reduce the production cost. There is no reaction step difficultly controlled during the preparation process, thus the industrialized production is easily realized.

In some embodiments, in step S1, a synthesis of Meldrum's acid comprises the following steps: under nitrogen protection, mixing acetic anhydride, malonic acid and an acid catalyst evenly by stirring, and then dripping acetone for reaction; cooling and crystallizing, performing suction filtration to obtain a filter cake, and drying to obtain Meldrum's acid.

In some embodiments, a weight ratio of acetic anhydride, malonic acid, acid catalyst to acetone is (210-240):(200-220):(8-15):(120-140); the acid catalyst is sulfuric acid or p-toluenesulfonic acid; a mixing time is 20-40 min; the temperature needs to be controlled at 20° C. or below when dripping acetone; a reaction temperature is 20-25° C.; the reaction is completed when a fractional conversion of malonic acid is greater than 99%; and the temperature needs to be reduced to −5° C. or below for cooling and crystallizing.

In the above technical solutions, in the present application, malonic acid, acetic anhydride and acetone are used as the raw materials to synthesize Meldrum's acid. This method is relatively simpler and the raw materials are easier to obtain, thus the production cost can be further reduced.

In step S1, the solvent is one selected from a group consisting of chloroform, dichloromethane and acetone; a weight ratio of Meldrum's acid, the solvent to the deacid reagent is (250-270):(1000-1500):(200-240); and a mole ratio of Meldrum's acid to the compound 1 is 1:(1-1.1). The deacid reagent is selected from one of triethylamine, pyridine and carbonate. A mixing time is 20-40 min, the temperature needs to be controlled at 0° C. or below when dripping compound 1; holding the temperature below 0° C. for 40-80 min; the reaction temperature is 20-25° C., and a reaction time is 18-24 h; and the pH is adjusted to 1-2 by adding hydrochloric acid.

In the above technical solutions, in the present application, by adjusting the reaction ratio of Meldrum's acid, compound 1 to deacid reagent, and controlling the reaction temperature and reaction time, the reaction can be conducted more complete, thus the yield of the intermediate E can be further improved.

In step S2, the solvent and the second batch of the solvent is one selected from a group consisting of benzene, methylbenzene, chloroform and xylene, and a weight ratio of the intermediate E to the solvent is (300-400):(1000-2000), and a mole ratio of the intermediate E to the compound 2 is 1:(1-1.2); the reaction temperature of heating reflux and water separation is 80-113° C., and the reaction time is 4-6 h; and a weight ratio of the solvent to the second batch of the solvent is (2-4):1.

In the above technical solutions, in the present application, by adjusting the ratio of the intermediate E to the compound 1, and controlling the reaction temperature and reaction time further, the reaction can be conducted more complete, and the occurrence of side reaction is reduced, which can improve the yield of the intermediate D. Additionally, the product in the present application undergoes the dissolved clarification, which can improve the purity of the intermediate D.

In step S3, a weight ratio of the intermediate D to acetic anhydride is (450-530):(500-600), and a mole ratio of the intermediate D to the compound 3 is 1:(0.5-1); and the heating is slow with a heating rate of 0.5-1° C./min, and an end temperature is 145° C.

In the above technical solutions, in the present application, by controlling the ratio of reaction substrates, the yield of the intermediate C can be improved. By adopting the process of simultaneous reaction and distillation, the low boiling substances can be distilled out, and the occurrence of the side reaction is reduced, which can not only improve the yield of the intermediate C, but also improve the purity of the intermediate C. The heating during the reaction process in the present application adopts the slow heating method, which can reduce and avoid a violent reaction. Avoiding the violent reaction can not only reduce the occurrence of the side reaction, but also reduce a requirement for an equipment, thereby reducing the production cost.

In step S4, the solvent is selected from any one of ethanol, acetone and chloroform; a weight ratio of the intermediate C, the solvent to methylhydrazine aqueous solution is (500-650):(900-1100):(130-200); the reaction temperature is 10-15° C., a time of holding the temperature for reaction is 0.5-1.5 h, a reflux temperature is 70-100° C., and a time of continuing reacting is 1-3 h.

In the above technical solutions, in the present application, by controlling the ratio of raw materials, the occurrence of the side reaction can be reduced; and by multi-stage temperature control, the reaction process can be controlled. Thus, the yield and purity of the product A can be improved.

In a second aspect, the present application provides the intermediates in the synthesis method for N-methyl-3-substituted methyl-4-pyrazolamide derivative, including the following intermediates:

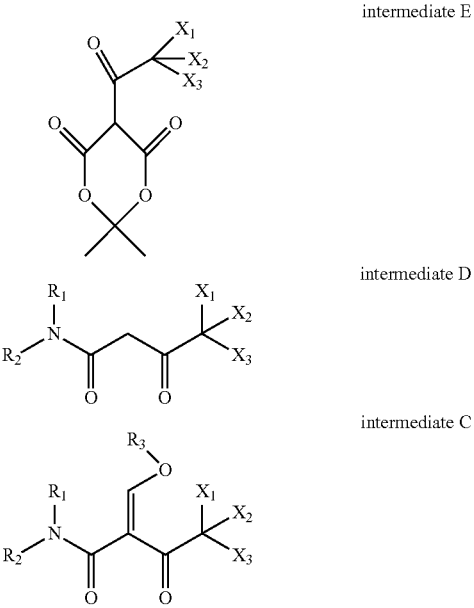

In the above technical solutions, the present application, by synthesizing the intermediate E, the intermediate D and the intermediate C described above, the synthesis of N-methyl-3-substituted methyl-4-pyrazolamide derivative can be simplified.

In a third aspect, the present application provides a synthesis method for N-methyl-3-substituted methyl-4-pyrazolic acid, including reacting the N-methyl-3-substituted methyl-4-pyrazolamide derivative A obtained according to the method in the above aspect with an acid to obtain the N-methyl-3-substituted methyl-4-pyrazolic acid. In some embodiments, the method includes the steps of: under nitrogen protection, adding N-methyl-3-substituted methyl-4-pyrazolamide derivative A and hydrochloric acid into water, raising the temperature to a reaction temperature for reflux reaction; after the reaction is completed, cooling to below 0° C.; and filtering and drying to obtain N-methyl-3-substituted methyl-4-pyrazolic acid B. In some embodiments, a weight ratio of N-methyl-3-substituted methyl-4-pyrazolamide derivative A to hydrochloric acid is (300-400):(150-250), a concentration of hydrochloric acid is 30%, a reaction temperature is 90-100° C., and a reaction time is 5-6 h.

The synthesis route is as follows:

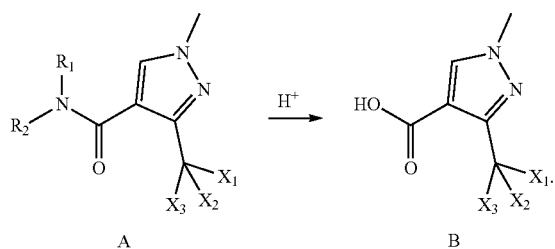

In the above technical solutions, N-methyl-3-substituted methyl-4-pyrazolamide derivative A synthesized in the present application can be reversely decomposed to synthesis N-methyl-3-substituted methyl-4-pyrazolic acid B, so that the synthesis process of N-methyl-3-substituted methyl-4-pyrazolic acid B can be simplified, and thus the synthesis cost can be reduced.

In summary, the present application has at least one of the following beneficial technical effects:
1. the present application provides the new synthesis method for N-methyl-3-substituted methyl-4-pyrazolamide derivative A, the raw materials are easily available, the synthesis route is short, and the requirement for each step of the synthesis process is not high, so that the industrialized production can be easily realized.
2. in the synthesis process of the present application, the intermediate E, the intermediate D and the intermediate C are synthesized, which can avoid the synthesis of N-methyl-3-substituted methyl-4-pyrazolic acid B, thus the synthesis process can be simplified.
3. in the present application, N-methyl-3-substituted methyl-4-pyrazolamide derivative A can be reversely decomposed synthesis to N-methyl-3-substituted methyl-4-pyrazolic acid B, so that the synthesis of N-methyl-3-substituted methyl-4-pyrazolic acid B can be further simplified, and thus the synthesis efficiency can be improved.

DETAILED DESCRIPTION

Figure 1:
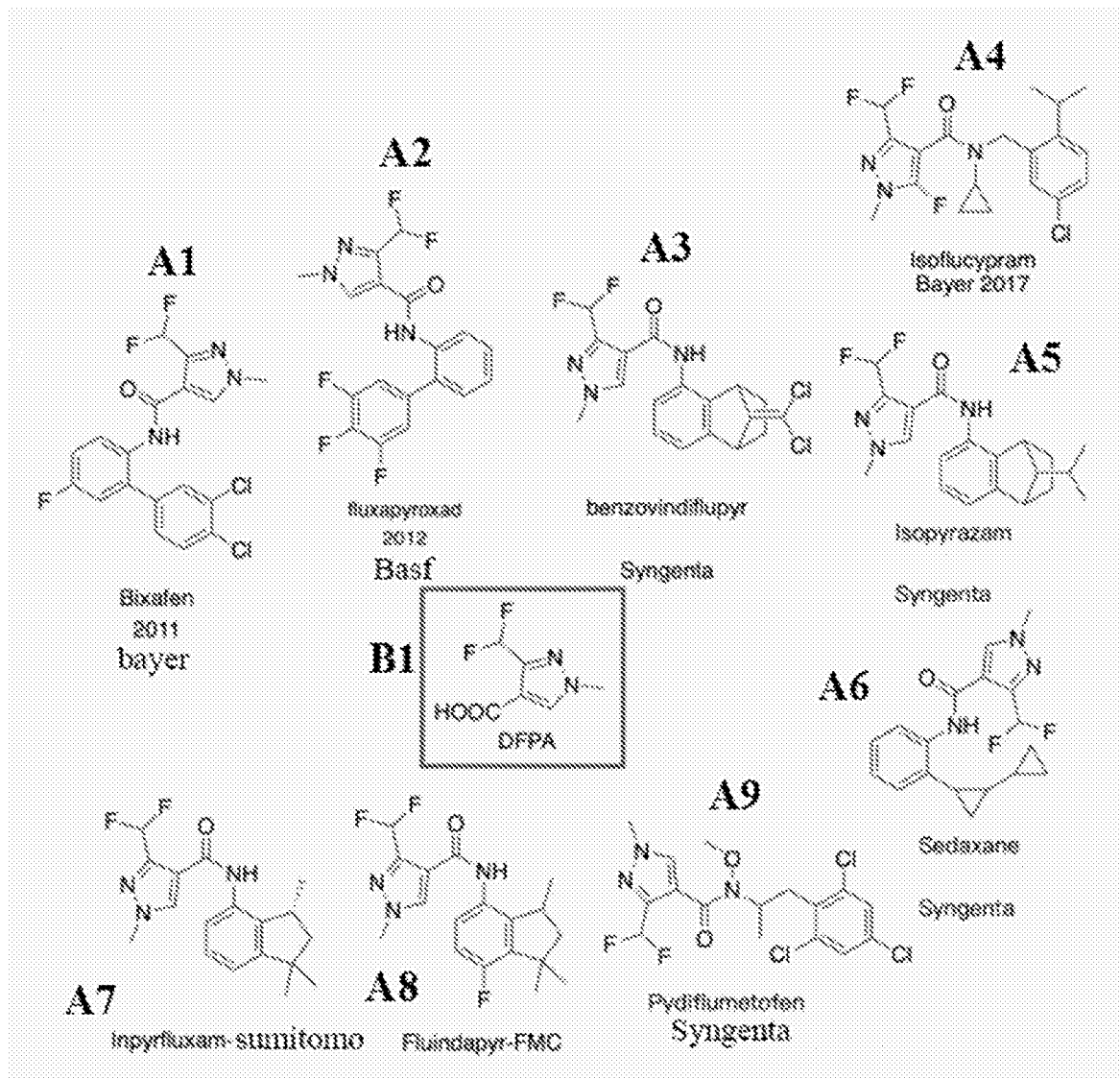
FIG. 1 illustrates the pesticide technical materials synthesized by N-methyl-3-substituted methyl-4-pyrazolic acid B in the background technology.
Figure 2:
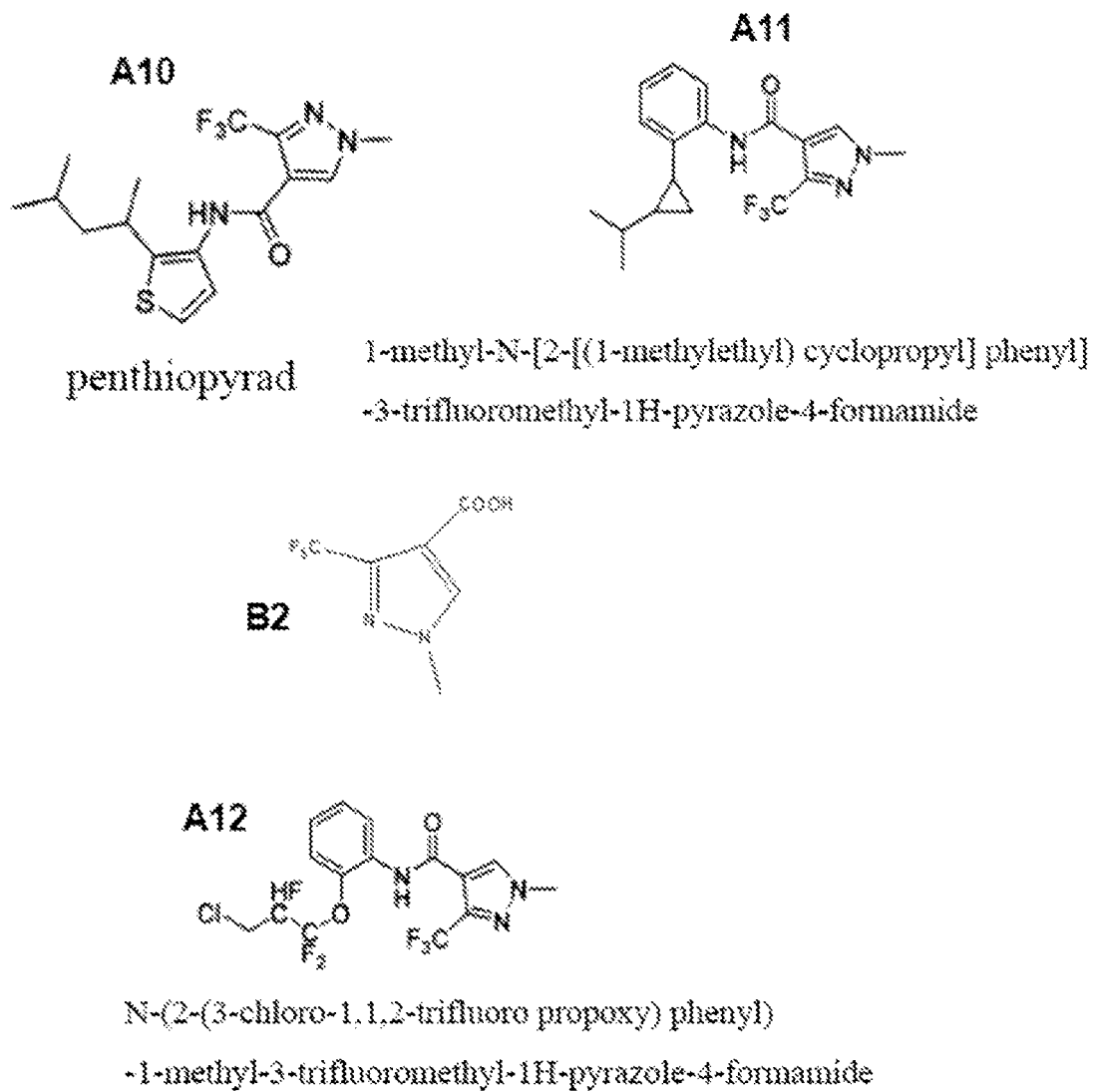
FIG. 2 illustrates the pesticide technical materials synthesized by N-methyl-3-substituted methyl-4-pyrazolic acid B in the background technology.
Figure 3:
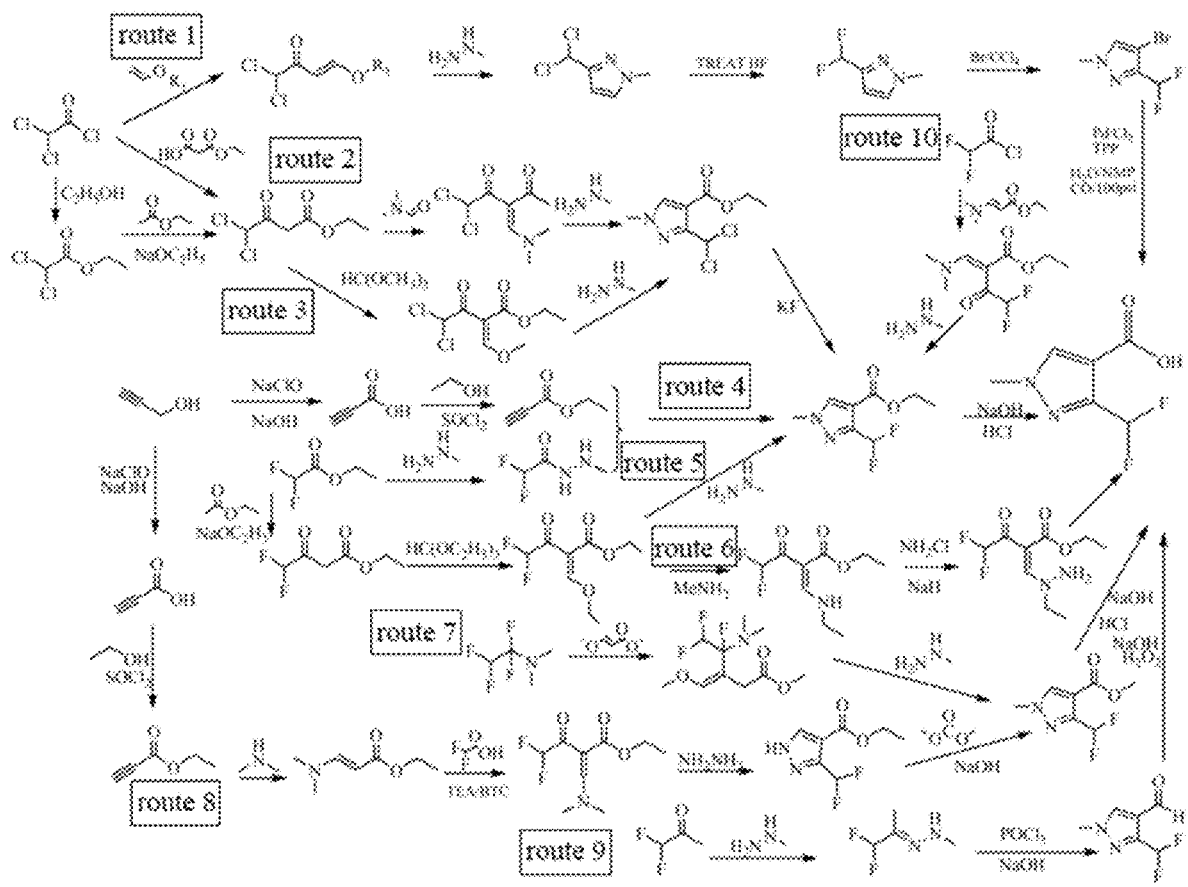
FIG. 3 illustrates multiple synthesis routes of N-methyl-3-substituted methyl-4-pyrazolic acid in the background.
Figure 4:
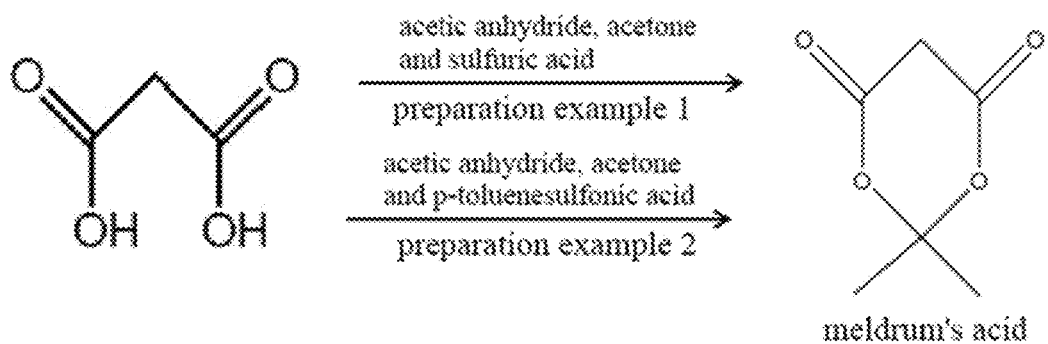
FIG. 4 illustrates the synthesis route of Meldrum's acid in preparation examples 1-2.

The synthesis route of Meldrum's acid is shown in FIG. 4, and the specific steps can refer to preparation examples 1 and 2.

Preparation Example 1

Under nitrogen protection, 227 g of acetic anhydride, 213 g of malonic acid and 12 g of sulfuric acid (mass concentration of 65%) were successively added into a reaction flask, and were stirred for about 30 min. A temperature was controlled at 15° C., and 128 g of acetone were dripped completely within about 2 h. After dripping completely, a reaction was performed at 22° C. for 1 h under a central control, and it was qualified when a fractional conversion of malonic acid was greater than 99%. After qualified, the temperature was reduced to below −5° C., and a crystallization was performed under stirring for 1 h. Then, a suction filtration was performed, the Meldrum's acid was obtained after drying a filter cake, and a yield was 82.9%.

Preparation Example 2

Under nitrogen protection, 227 g of acetic anhydride, 213 g of malonic acid and 13 g of p-toluenesulfonic acid were successively added into the reaction flask, and were stirred for about 30 min. The temperature was controlled at 10° C., and 128 g of acetone were dripped completely within about 2 h. After dripping completely, the reaction was performed at 24° C. for about 1 h under the central control, and it was qualified when the fractional conversion of malonic acid was greater than 99%. After qualified, the temperature was reduced to below −5° C., and the crystallization was performed under stirring for 1 h. Then, the suction filtration was performed, the Meldrum's acid was obtained after drying a filter cake, and the yield was 87.2%.

Figure 5:
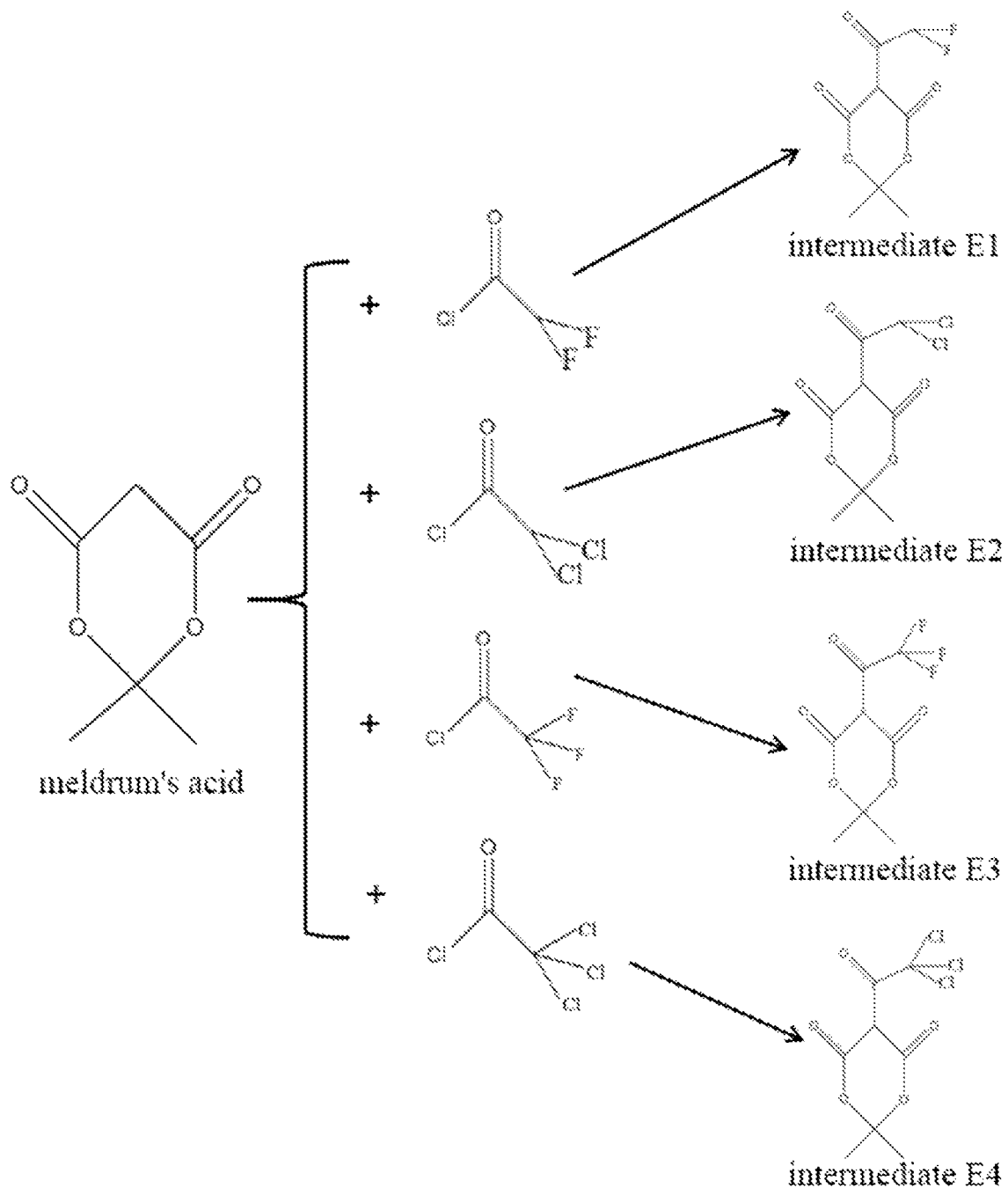
FIG. 5 illustrates the synthesis routes of intermediates E1-E4 in preparation examples 3-6.

The synthesis routes of intermediates E1-E4 are shown in FIG. 5, and the specific preparation process can refer to preparation examples 3-6.

Preparation Example 3

Under nitrogen protection, 1300 g of chloroform and 265 g of Meldrum's acid (prepared in preparation example 1) were successively added into the reaction flask. The temperature was reduced to below 0° C., and 223 g of triethylamine was dripped completely within about 1 h. After dripping completely, the stirring was performed for 30 min under a condition of holding the temperature. Then, 210 g of difluoroacetyl chloride were dripped completely within about 2 h under a condition that the temperature was controlled below 0° C. After dripping completely, the temperature was kept for 1 h, then was raised to 23° C., and the reaction under the condition of holding the temperature was performed for 20 h under the central control. A reaction endpoint was the fractional conversion of Meldrum's acid greater than 99%. After qualified, hydrochloric acid was dripped to adjust pH=1-2. After qualified, the stirring was performed for 30 min, and a standing is performed to separate into layers. An organic phase was washed twice with a saturated saline water, and the standing is performed to separate into layers. The organic phase undergone a solvent removing under reduced pressure, and was cooled to a room temperature. Then, the intermediate E1 was obtained, and the yield was 85.5%.

Preparation Example 4

It was basically the same as preparation example 3, with the difference being that: 210 g of difluoroacetyl chloride was replaced with 270 g of dichloroacetyl chloride, and Meldrum's acid was prepared in preparation example 2; and the intermediate E2 was obtained, and the yield was 84.7%.

Preparation Example 5

It was basically the same as preparation example 3, with the difference being that: 210 g of difluoroacetyl chloride was replaced with 243 g of trifluoroacetyl chloride, 223 g triethylamine was replaced with 175 g pyridine, and Meldrum's acid was purchased directly; and the intermediate E3 was obtained, and the yield was 86.2%.

Preparation Example 6

It was basically the same as preparation example 5, with the difference being that: 243 g of trifluoroacetyl chloride was replaced with 334 g of trichloroacetyl chloride, and the intermediate E4 was obtained.

Example 1 Preparation of BixafenA1

Figure 6:
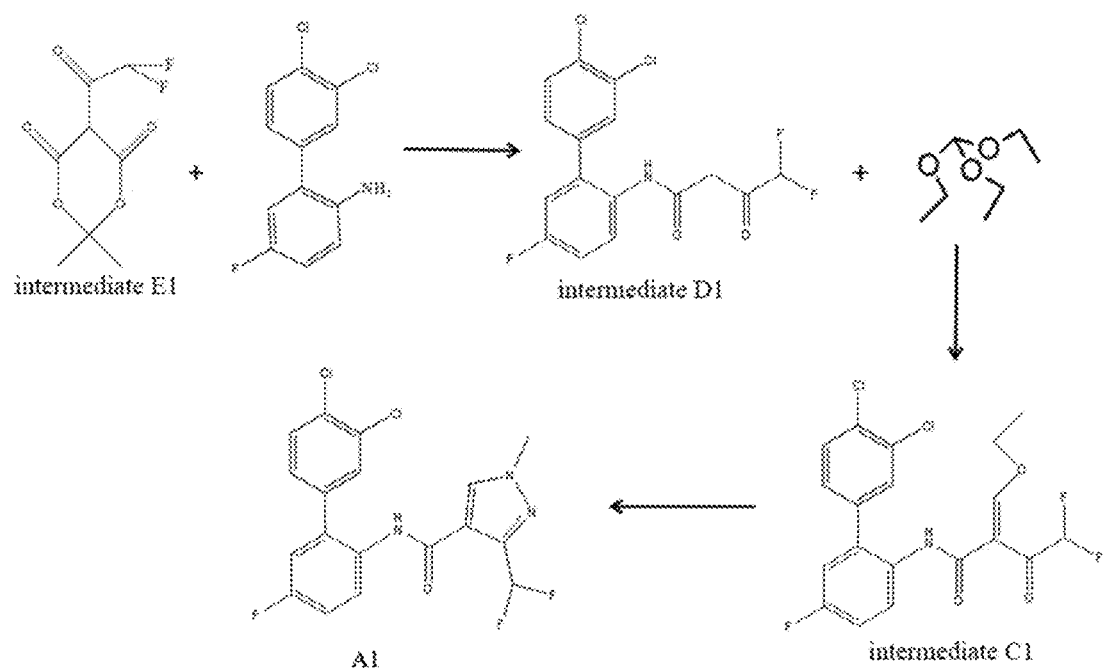
FIG. 6 illustrates the synthesis route of product A1 in example 1.

The synthesis route is shown in FIG. 6 and specifically includes the following steps:

Under nitrogen protection, 1450 g of methylbenzene, 368 g of intermediate E1 prepared in preparation example 3 and 424 g of O (3,4-dichlorophenyl)-4-fluoroaniline were successively added into the reaction flask. The temperature was raised to 100° C., a reflux and water separation was performed for 5 h. After the central control is qualified, the solvent removing under reduced pressure was performed, and 500 g of methylbenzene was added to a residual. After heating and dissolved clarification, the temperature was reduced to below 0° C., and the crystallization was performed under stirring for 2 h. Then, a filtration was performed, an intermediate D1 was obtained after drying the filter cake, and the yield was 87.9%.

Under nitrogen protection, 508 g of acetic anhydride, 561 g of intermediate D1 and 270 g of triethylorthoformate were successively added into the reaction flask. The heating reflux was performed at a heating rate of 0.5° C./min, and the reaction was performed while distilling a low boiling substance. An endpoint temperature was controlled at 145° C., which takes about 6 h. After the central control is qualified, the temperature was reduced to about 80° C., a vacuum distillation was performed to remove the residual acetic anhydride, and 500 g of ethanol was added to the residual. After heating and dissolved clarification, the temperature was reduced to below 0° C., and the crystallization was performed under stirring. Then, the filtration was performed, an intermediate C1 was obtained after drying the filter cake, and the yield was 85.4%.

Under nitrogen protection, 1108 g of ethanol and 582 g of intermediate C1 were successively added into the reaction flask. The temperature was controlled at 15° C., and 174 g of methylhydrazine aqueous solution was dripped completely within about 3 h. After dripping completely, the temperature was kept for 1 h under stirring, then was raised to 80° C. for the reflux for 2 h. After the central control is qualified, the solvent removing under reduced pressure was performed. Then, the temperature was reduced to below 0° C., and the filtration was performed. After drying, a fluxapyroxad A1 was obtained, and the yield was 80.5%.

Example 2

Figure 7:
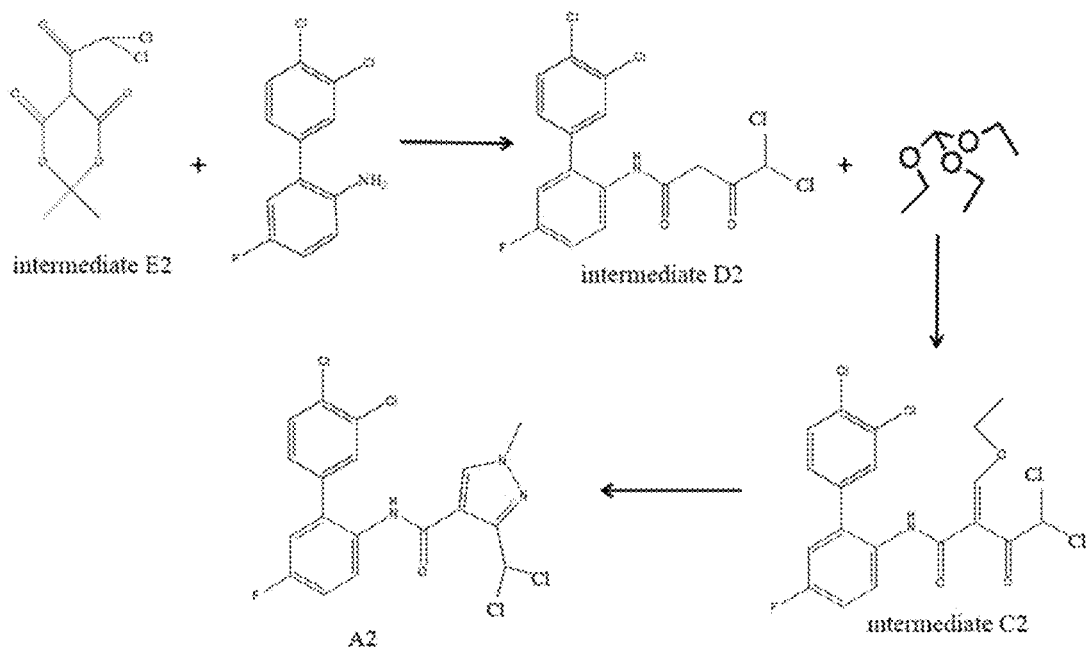
FIG. 7 illustrates the synthesis route of product A2 in example 2.

The synthesis route is shown in FIG. 7, and the specific steps were basically the same as example 1, except for the use of intermediate E2, thus an intermediate D2 (yield of 82.7%), an intermediate C2 (yield of 84.4%), and a final product A2 (yield of 81.5%) were obtained correspondingly.

Example 3

Figure 8:
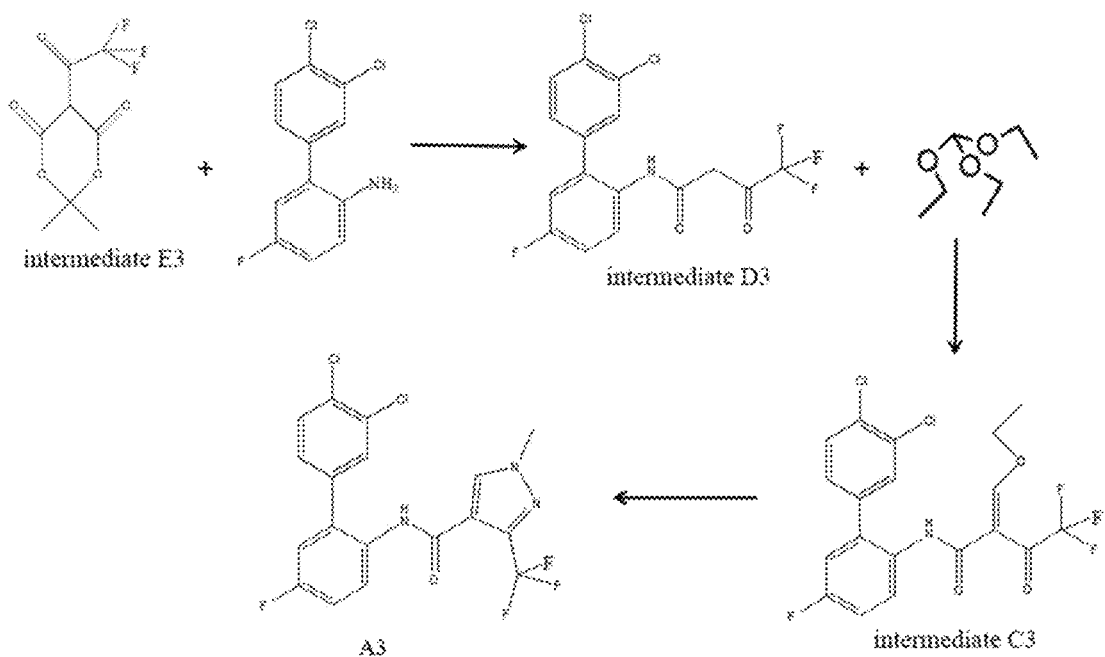
FIG. 8 illustrates the synthesis route of product A3 in example 3.
Figure 9:
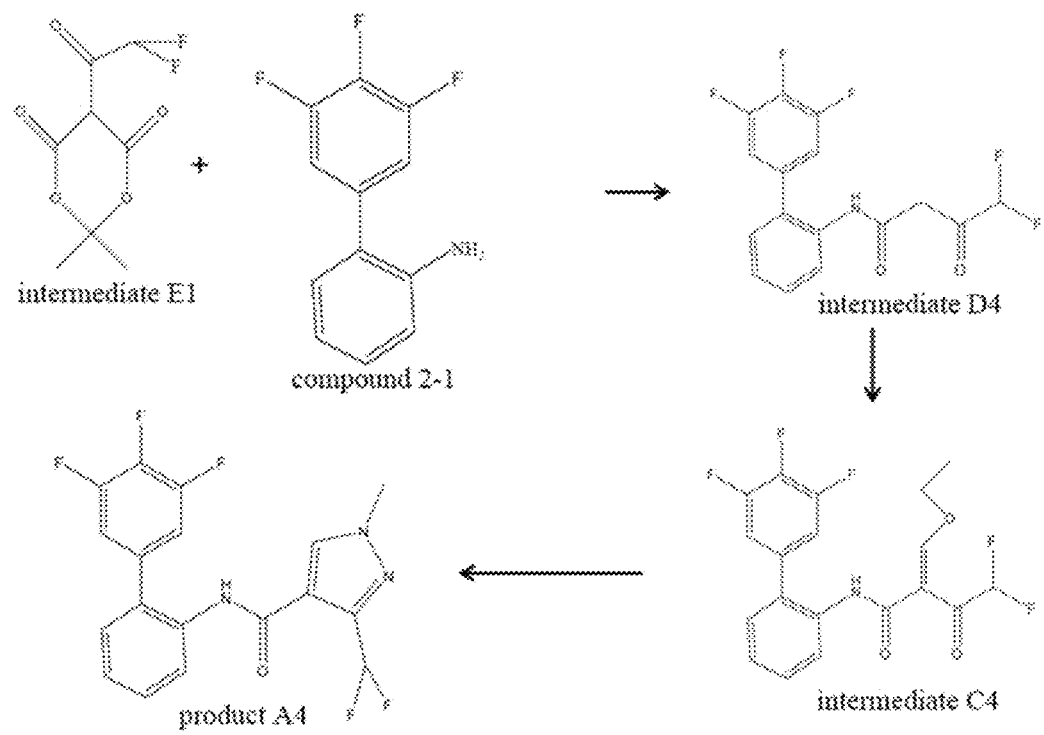
FIGS. 9-16 respectively illustrate the synthesis route of products A4-11 in examples 4-11.
Figure 10:
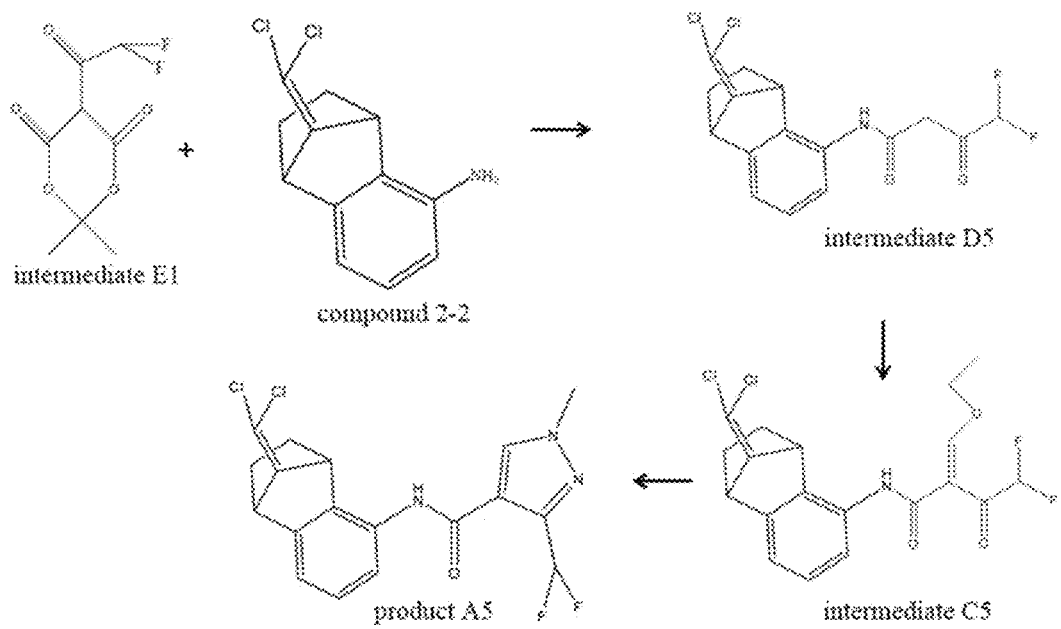
Figure 11:
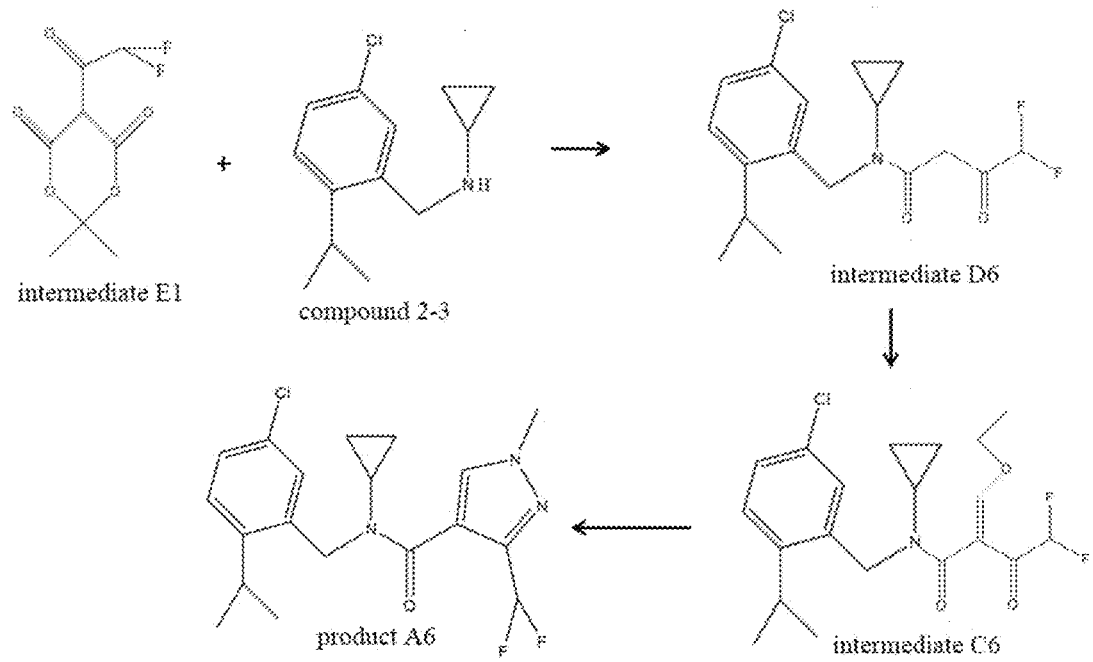

The synthesis route is shown in FIG. 8, and the specific steps were basically the same as example 1, except for the use of intermediate E3, thus an intermediate D3 (yield of 84.6%), an intermediate C3 (yield of 85.7%), and a final product A3 (yield of 81.2%) were obtained correspondingly.

Changes in a weight of raw materials for each step in examples 2-3 can be seen in Table 1.

TABLE 1

|  | intermediate E2 | intermediate D2 | intermediate C2 |
|---|---|---|---|
| Example 2 | 422 g | 610 g | 626 g |
|  | intermediate E3 | intermediate D3 | intermediate C3 |
| Example 3 | 399 g | 588 g | 606 g |

Examples 4-11

The synthesis routes of examples 4-11 are shown in FIGS. 9-16 respectively, and were basically the same as example 1. Differences lies in that O (3,4-dichlorophenyl)-4-fluoroaniline was replaced with compounds 2-1 to 2-8 respectively, so that intermediates D4-11 and intermediates C4-11 were obtained correspondingly, and thus products A4-11 were obtained correspondingly. The changes in the weight of raw materials in each step and the yield in each step can be seen in Table 2:

TABLE 2

| Example 4 | | | | | |
|---|---|---|---|---|---|
| Compound 2-1 | Yield of intermediate D4 | Intermediate D4 | Yield of intermediate C4 | Intermediate C4 | Yield of product A4 |
| 369 g | 88.2% | 513 g | 84.7% | 539 g | 85.4% |

TABLE 2-continued

| Example 5 | | | | | |
|---|---|---|---|---|---|
| Compound 2-2 | Yield of intermediate D5 | Intermediate D5 | Yield of intermediate C5 | Intermediate C5 | Yield of product A5 |
| 397 g | 87.3% | 537 g | 84.6% | 560 g | 84.5% |
| Example 6 | | | | | |
| Compound 2-3 | Yield of intermediate D6 | Intermediate D6 | Yield of intermediate C6 | Intermediate C6 | Yield of product A6 |
| 370 g | 82.7% | 513 g | 86.9% | 539 g | 85.6% |
| Example 7 | | | | | |
| Compound 2-4 | Yield of intermediate D7 | Intermediate D7 | Yield of intermediate C7 | Intermediate C7 | Yield of product A7 |
| 329 g | 87.5% | 476 g | 82.4% | 505 g | 86.2% |
| Example 8 | | | | | |
| Compound 2-5 | Yield of intermediate D8 | Intermediate D8 | Yield of intermediate C8 | Intermediate C8 | Yield of product A8 |
| 286 g | 90.2% | 437 g | 85.1% | 470 g | 87.4% |
| Example 9 | | | | | |
| Compound 2-6 | Yield of intermediate D9 | Intermediate D9 | Yield of intermediate C9 | Intermediate C9 | Yield of product A9 |
| 444 g | 81.3% | 579 g | 87.9% | 598 g | 88.5% |
| Example 10 | | | | | |
| Compound 2-7 | Yield of intermediate D10 | Intermediate D10 | Yield of intermediate C10 | Intermediate C10 | Yield of product A10 |
| 320 g | 85.4% | 467 g | 84.2% | 497 g | 90.4% |
| Example 11 | | | | | |
| Compound 2-8 | Yield of intermediate D11 | Intermediate D11 | Yield of intermediate C11 | Intermediate C11 | Yield of product A11 |
| 320 g | 78.9% | 467 g | 83.6% | 497 g | 86.3% |

Example 12

Figure 12:
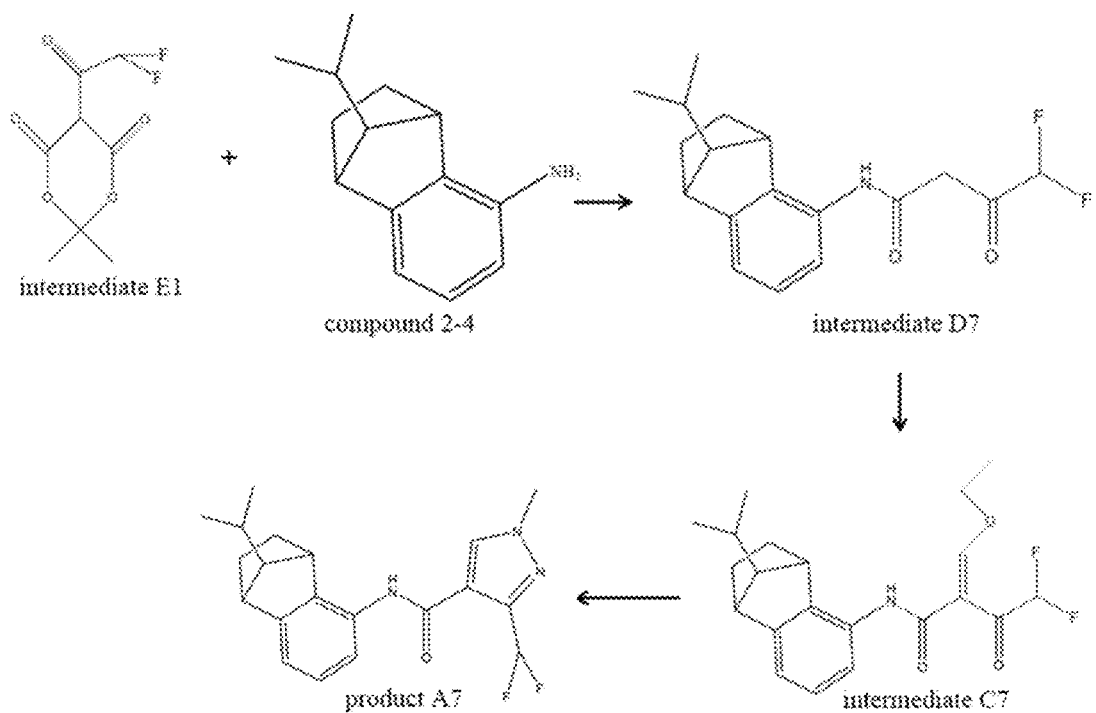
Figure 13:
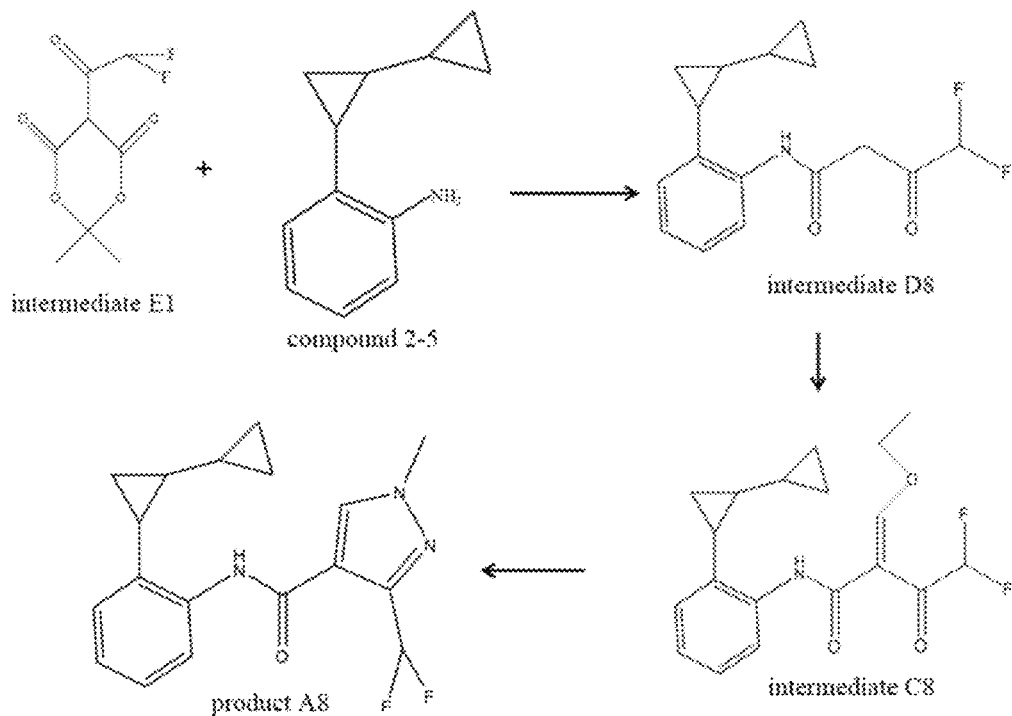
Figure 14:
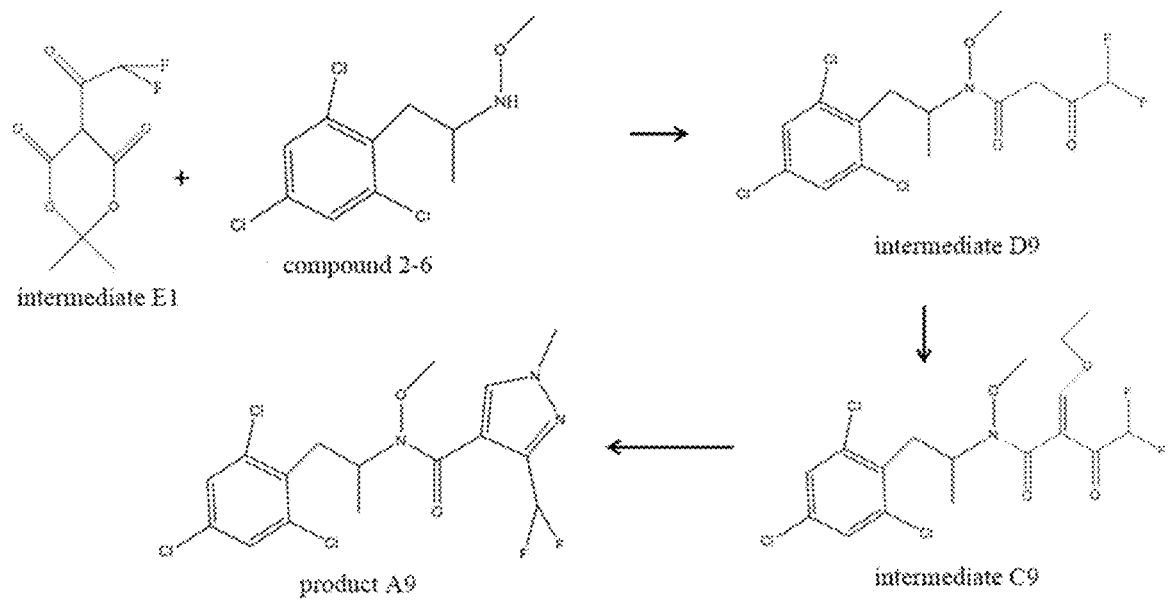
Figure 15:
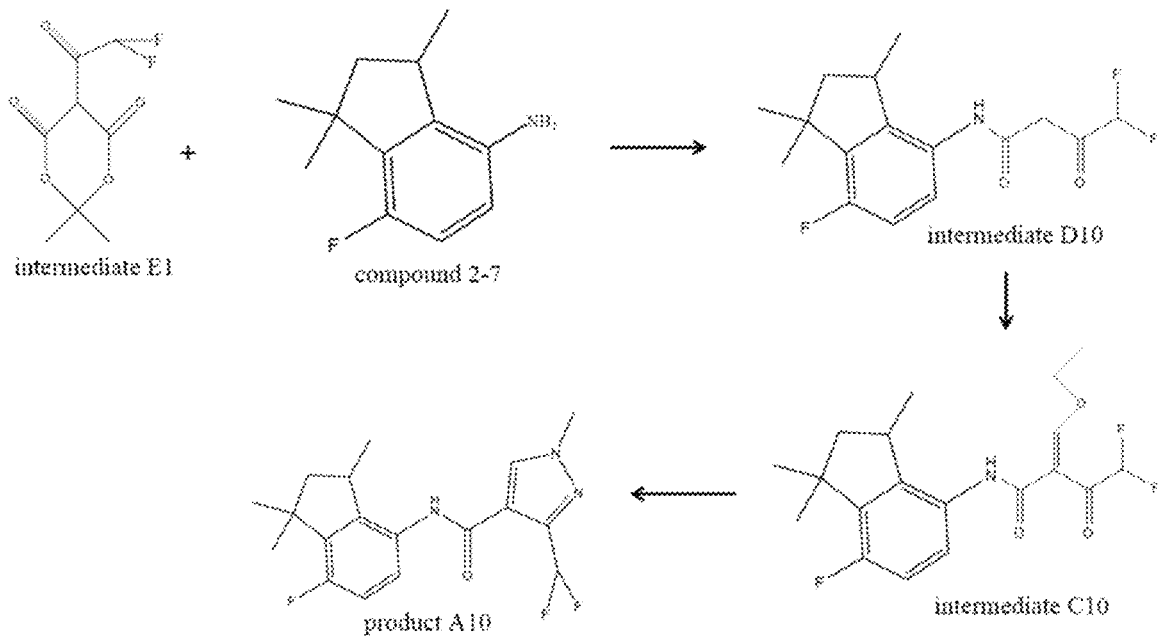
Figure 16:
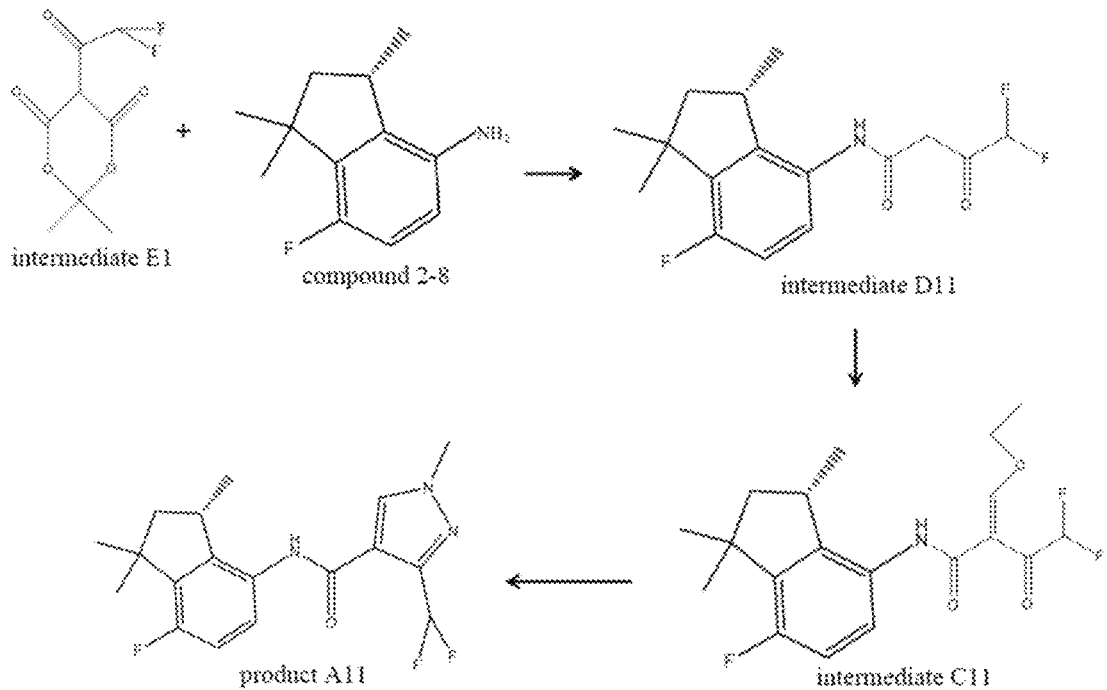
Figure 17:
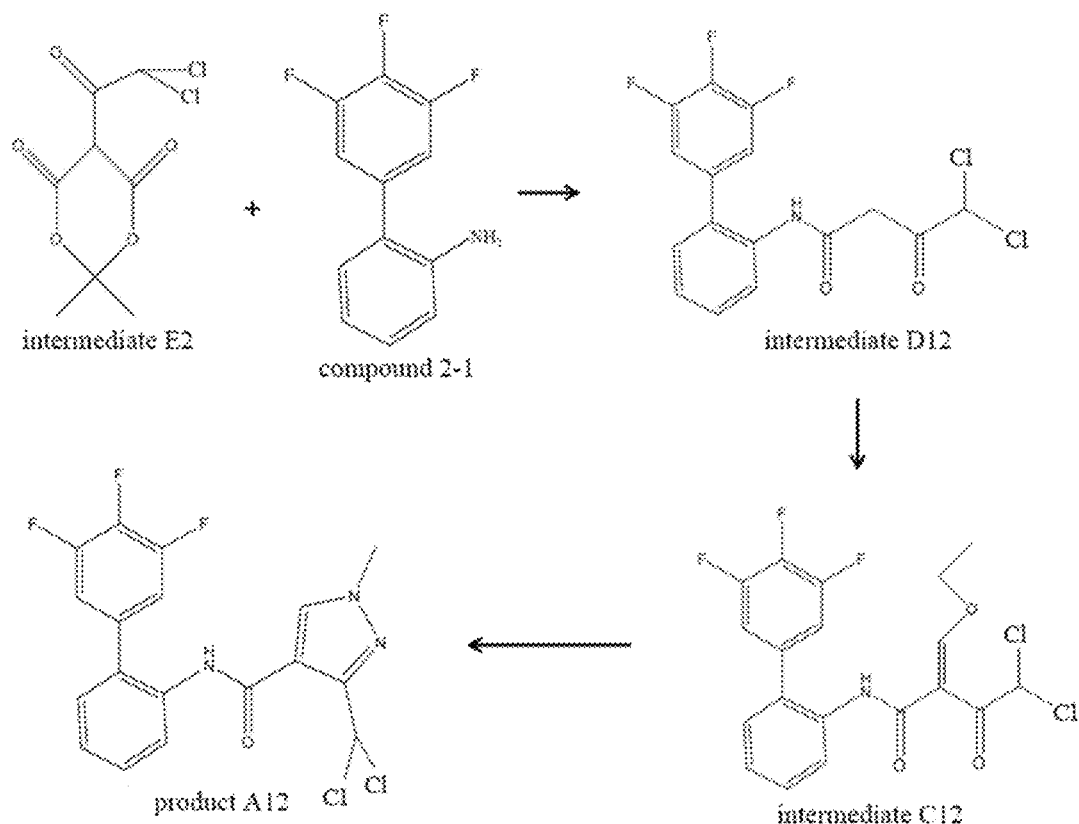
FIG. 17 illustrates the synthesis route in example 12.

The synthesis route of example 12 is shown in FIG. 12, and was basically the same as example 2. Differences lies in that O (3,4-dichlorophenyl)-4-fluoroaniline was replaced with compound 2-1, so that an intermediate D12 and an intermediate C12 were obtained correspondingly, and thus a product A12 was obtained correspondingly. The changes in the weight of raw materials in each step and the yield in each step can be seen in Table 3:

Examples 13-15

Figure 18:
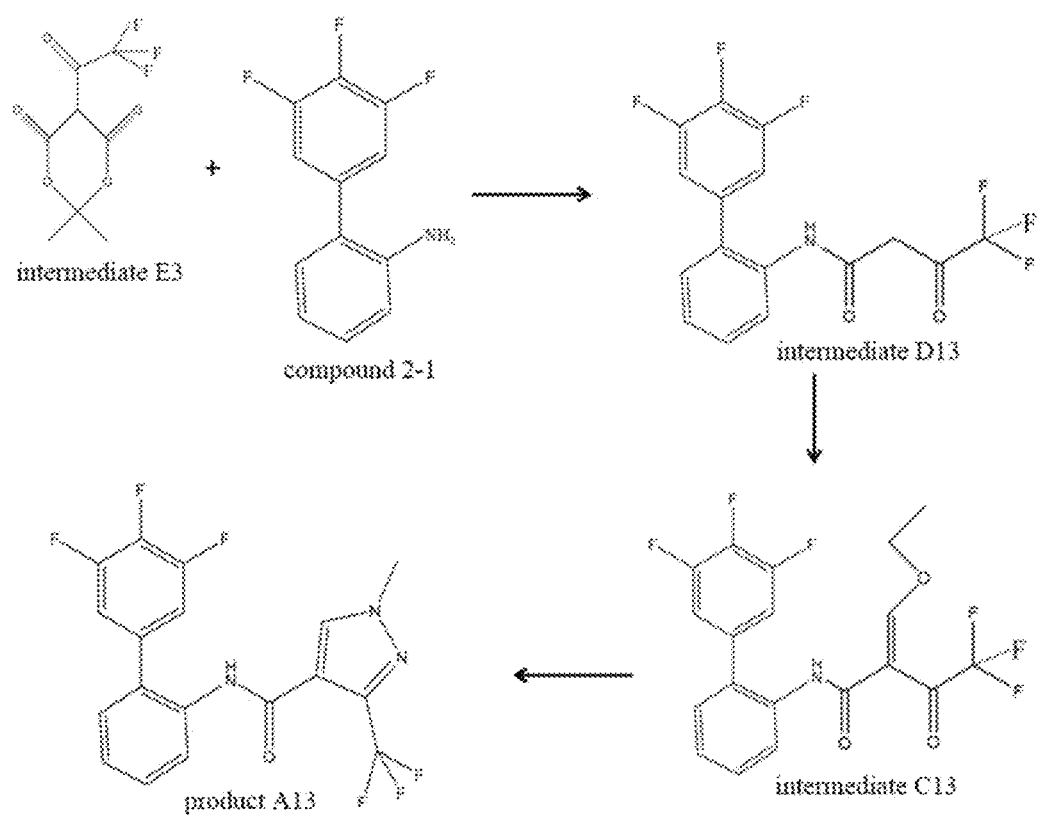
FIGS. 18-20 respectively illustrate the synthesis route of products A13-15 in examples 13-15.
Figure 19:
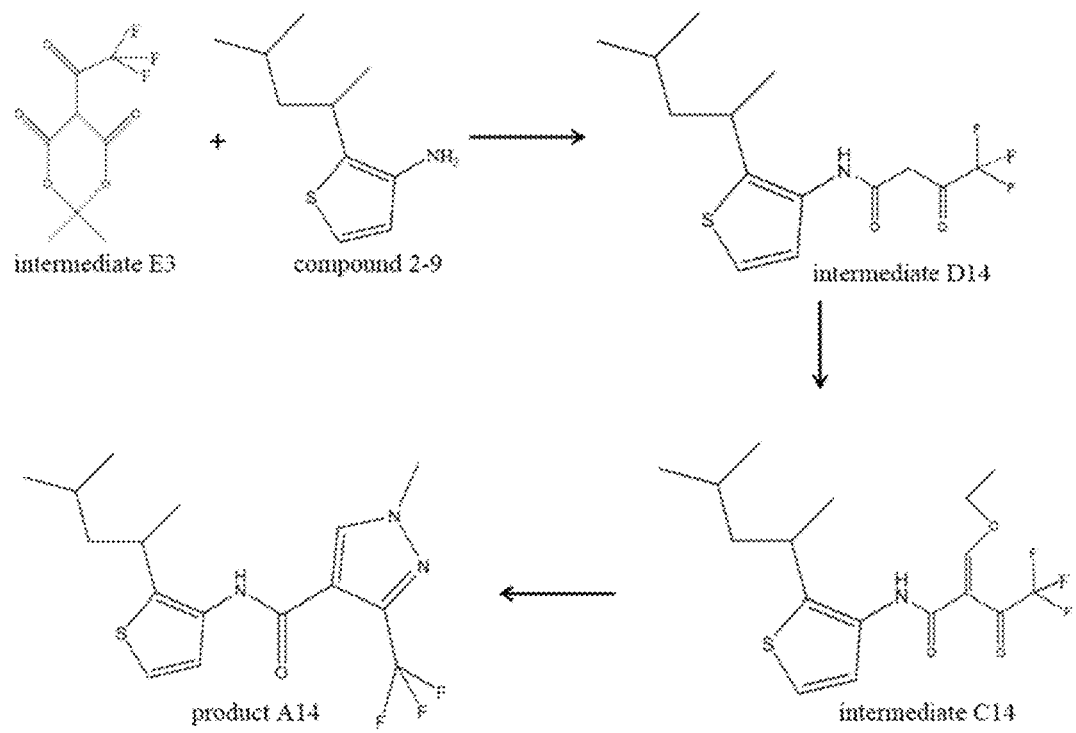
Figure 20:
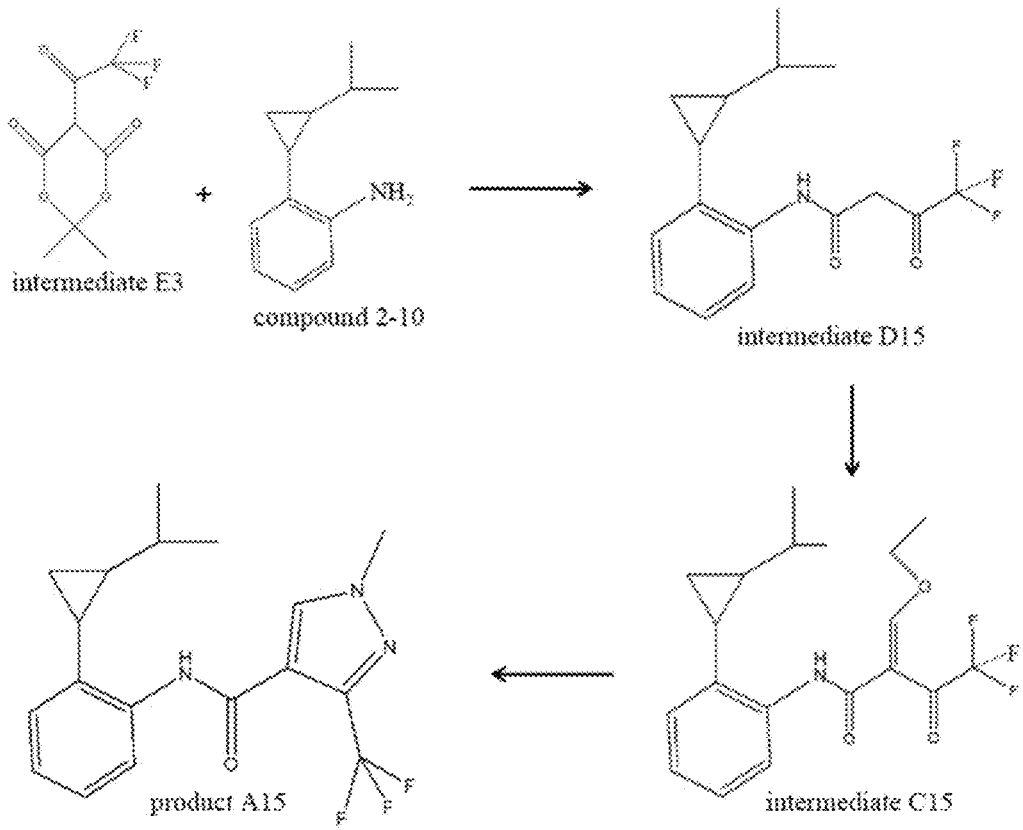

The synthesis routes of examples 13-15 are shown in FIGS. 18-20 respectively, and were basically the same as example 3. Differences lies in that O (3,4-dichlorophenyl)-4-fluoroaniline was replaced with compound 2-1, compound 2-9 and compound 2-10 respectively, so that intermediates D13-15 and intermediates C13-15 were obtained correspondingly, and thus products A13-15 were obtained correspondingly.

The changes in the weight of raw materials in each step and the yield in each step can be seen in Table 4:

TABLE 3

| Example 12 | | | | | |
|---|---|---|---|---|---|
| Compound 2-1 | Yield of intermediate D12 | Intermediate D12 | Yield of intermediate C12 | Intermediate C12 | Yield of intermediate A12 |
| 369 g | 86.4.2% | 576 g | 82.6% | 595 g | 87.4% |

TABLE 4

| Example 13 | | | | | |
|---|---|---|---|---|---|
| Compound 2-1 | Yield of intermediate D13 | Intermediate D13 | Yield of intermediate C13 | Intermediate C13 | Yield of product A13 |
| 369 g | 88.2% | 553 g | 84.7% | 575 g | 85.4% |
| Example 14 | | | | | |
| Compound 2-9 | Yield of intermediate D14 | Intermediate D14 | Yield of intermediate C14 | Intermediate C14 | Yield of product A14 |
| 303 g | 86.4% | 479 g | 82.9% | 508 g | 85.7% |
| Example 15 | | | | | |
| Compound 2-10 | Yield of intermediate D15 | Intermediate D15 | Yield of intermediate C15 | Intermediate C15 | Yield of product A15 |
| 290 g | 81.7% | 467 g | 85.9% | 497 g | 88.6% |

Examples 16-19

Intermediates B1-B4 were prepared by synthesizing products A16-19 and then decomposing A16-19.

Figure 21:
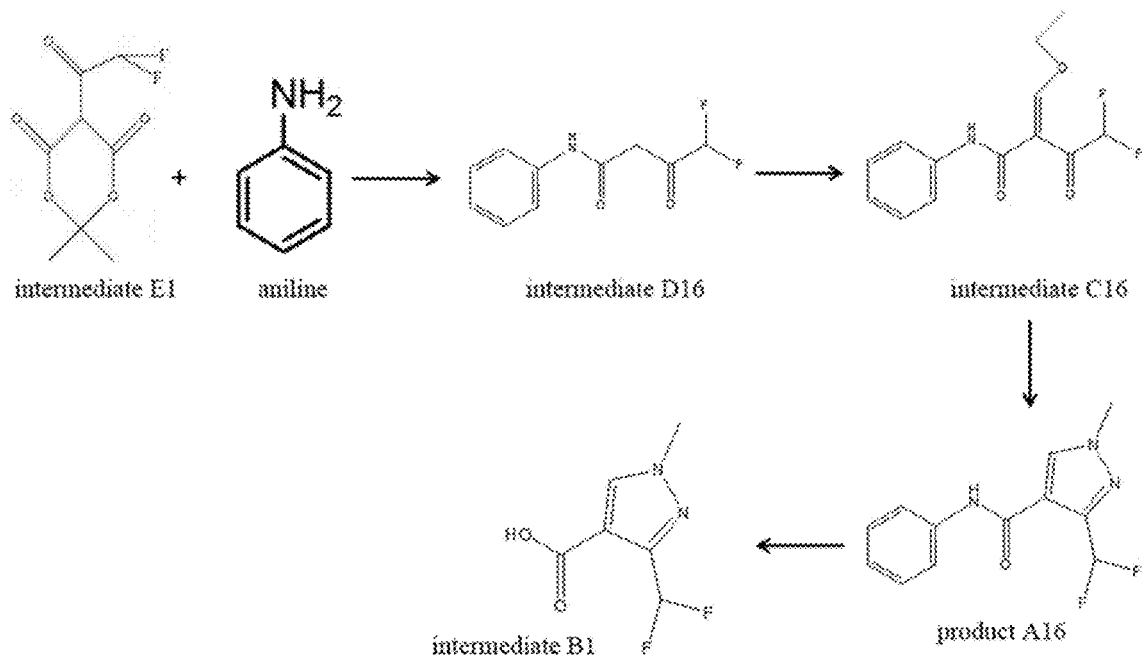
FIGS. 21-24 respectively illustrate the synthesis route of products A16-19 and intermediates B1-4 in examples 16-19.

Example 16: a synthesis process for product A16 was basically the same as example 1, except that the o (3,4-dichlorophenyl)-4-fluoroaniline was replaced with aniline, as shown in FIG. 21.

| Example 16 | | | | | |
|---|---|---|---|---|---|
| Aniline | Yield of intermediate D16 | Intermediate D16 | Yield of intermediate C16 | Intermediate C16 | Yield of product A16 |
| 154 g | 89.2% | 317 g | 87.6% | 362 g | 90.4% |

A preparation process for intermediate B1 is as follows: under nitrogen protection, 800 g of water, 303 g of the product A16 and 200 g of hydrochloric acid (30%) were added into the reaction flask. Then, the temperature was raised to 100° C. for the reflux for 2 h. After the central control is qualified, the temperature was reduced to below 0° C., and the filtration was performed. After drying, a compound B1 (N-methyl-3-difluoromethyl-4-pyrazolic acid) was obtained, and the yield was 85.4%.

Figure 22:
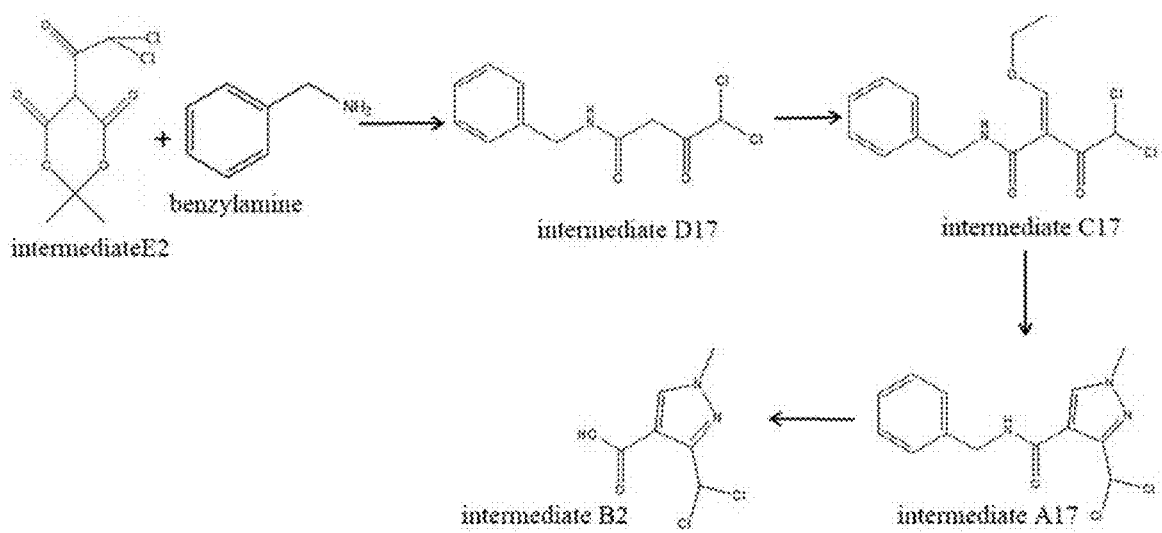

Example 17: a synthesis process for product A17 was basically the same as example 16, except that the intermediate E1 was replaced with intermediate E2, and aniline was replaced with benzylamine, as shown in FIG. 22.

| Example 17 | | | | | | |
|---|---|---|---|---|---|---|
| benzylamine | Intermediate E2 | Yield of intermediate D17 | Intermediate D17 | Yield of intermediate C17 | Intermediate C17 | Yield of product A17 |
| 177 g | 422 g | 88.9% | 369 g | 89.3% | 407 g | 87.4% |

A preparation process for intermediate B2 is as follows: under nitrogen protection, 600 g of water, 258 g of the product A17 and 154 g of hydrochloric acid (30%) were added into the reaction flask. Then, the temperature was raised to 100° C. for the reflux for 6 h. After the central control is qualified, the temperature was reduced to below 0° C., and the filtration was performed. After drying, the compound B2 (N-methyl-3-difluoromethyl-4-pyrazolic acid) was obtained, and the yield was 86.4%.

Figure 23:
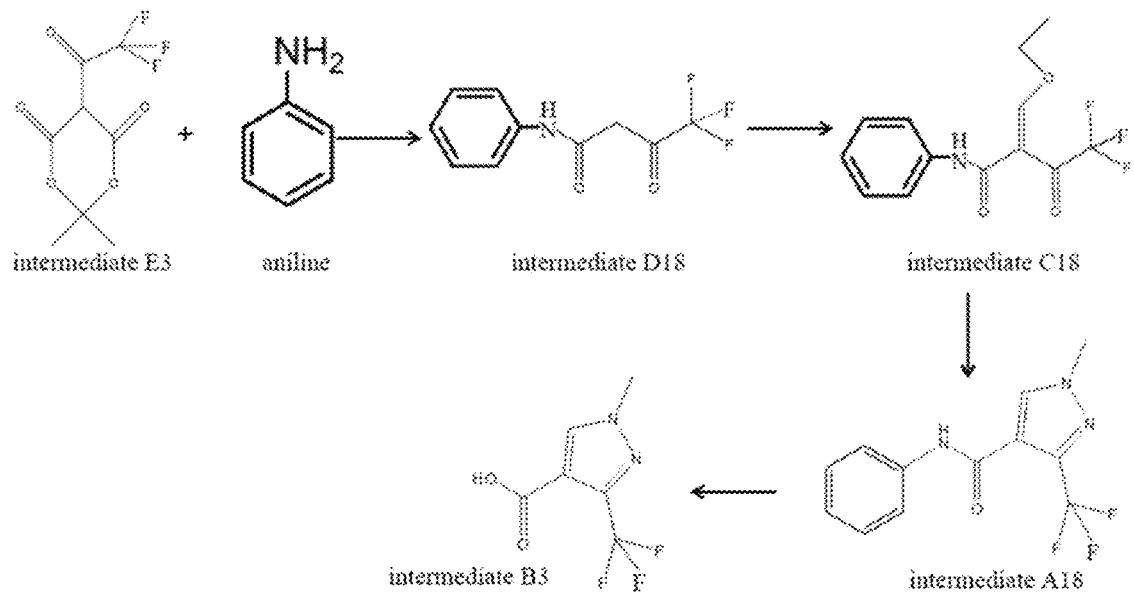

Example 18: a synthesis process for product A18 was basically the same as example 16, except that the intermediate E1 was replaced with intermediate E3, as shown in FIG. 23.

| Example 18 | | | | | |
|---|---|---|---|---|---|
| Intermediate E3 | Yield of intermediate D18 | Intermediate D18 | Yield of intermediate C18 | Intermediate C18 | Yield of product A18 |
| 399 g | 89.8% | 345 g | 87.9% | 387 g | 88.6% |

A preparation process for intermediate B3 is as follows: under nitrogen protection, 800 g of water, 301 g of the product A18 and 196 g of hydrochloric acid (30%) were added into the reaction flask. Then, the temperature was raised to 100° C. for the reflux for 6 h. After the central control is qualified, the temperature was reduced to below 0° C., and the filtration was performed. After drying, the compound B3 (N-methyl-3-difluoromethyl-4-pyrazolic acid) was obtained, and the yield was 84.9%.

Figure 24:
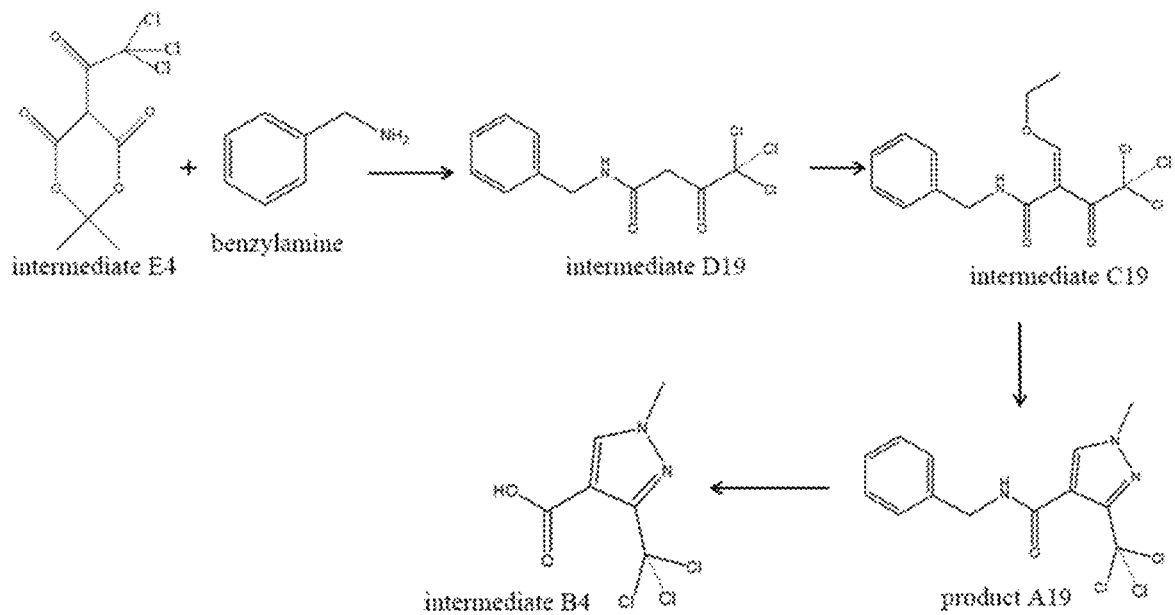

Example 19: a synthesis process for product A19 was basically the same as example 17, except that the intermediate E2 was replaced with intermediate E4, as shown in FIG. 24.

| Example 19 | | | | | |
|---|---|---|---|---|---|
| Intermediate E4 | Yield of intermediate D19 | Intermediate D19 | Yield of intermediate C19 | Intermediate C19 | Yield of product A19 |
| 479 g | 88.8% | 418 g | 88.5% | 453 g | 87.8% |

A preparation process for intermediate B4 is as follows: under nitrogen protection, 800 g of water, 314 g of the product A19 and 240 g of hydrochloric acid (30%) were added into the reaction flask. Then, the temperature was raised to 100° C. for the reflux for 6 h. After the central control is qualified, the temperature was reduced to below 0° C., and the filtration was performed. After drying, the compound B4 (N-methyl-3-difluoromethyl-4-pyrazolic acid) was obtained, and the yield was 87.6%.

The above are the preferred embodiments of the present application, which are not intended to limit the protection scope of the present application. Therefore, all equivalent changes made according to the structure, shape and principle of the present application should be covered within the protection scope of the present application.

What is claimed is:

1. A synthesis method for N-methyl-3-substituted methyl-4-pyrazolamide derivative A, comprising a synthesis route of:

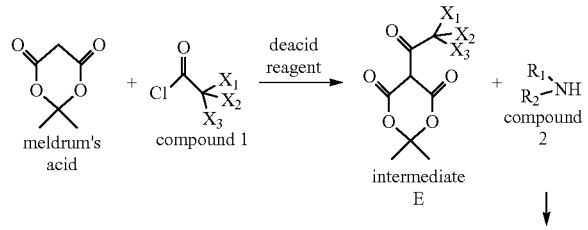

-continued

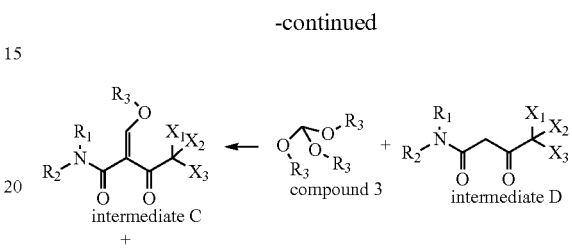

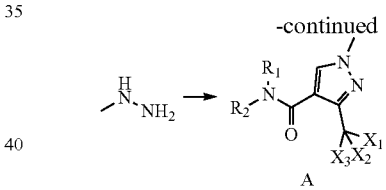

where, X1, X2 and X3 are one selected from a group consisting of H, F, Cl and Br, respectively; R1 and R2 are one selected from a group consisting of H, 1-4 benzene rings or substituted benzene rings, and aliphatic hydrocarbon group with 1-8 carbon atoms, respectively, and R3 is an aliphatic group having 1-4 carbon atoms.

2. The synthesis method for N-methyl-3-substituted methyl-4-pyrazolamide derivative A according to claim 1, wherein step S1 for synthesis of an intermediate E comprises: under protection of nitrogen, adding Meldrum's acid into a first solvent, cooling to 0° C. or below, adding a deacid reagent dropwise, stirring, adding the compound 1 to create a reaction solution, holding a temperature at 0° C. or below, raising the temperature to a reaction temperature for reaction, adding hydrochloric acid into the reaction solution to adjust pH, standing for separation into layers to obtain an organic phase, and subjecting the organic phase to solvent removing under a pressure to obtain the intermediate E.

3. The synthesis method for N-methyl-3-substituted methyl-4-pyrazolamide derivative A according to claim 2, wherein, a synthesis of the Meldrum's acid comprises the following steps: under the protection of nitrogen, mixing acetic anhydride, malonic acid and an acid catalyst evenly under stirring, adding acetone dropwise for reaction, cooling, crystallizing, performing suction filtration to obtain a filter cake, and drying to obtain the Meldrum's acid.

4. The synthesis method for N-methyl-3-substituted methyl-4-pyrazolamide derivative A according to claim 3, wherein, a weight ratio of the acetic anhydride to the malonic acid to the acid catalyst to the acetone is (210-240):(200-220):(8-15):(120-140); the acid catalyst is one selected from a group consisting of sulfuric acid or p-toluenesulfonic acid; a mixing time is 20-40 min; the temperature is controlled below 20° C. when adding the acetone dropwise; a reaction temperature when adding the acetone dropwise is 20-25° C.; the reaction is terminated when a fractional conversion of the malonic acid is greater than 99%; and the temperature is reduced to below −5° C. for the cooling and the crystallizing.

5. The synthesis method for N-methyl-3-substituted methyl-4-pyrazolamide derivative A according to claim 2, wherein, in step S1, the first solvent is one selected from a group consisting of chloroform, dichloromethane and acetone; and the deacid reagent is one selected from a group consisting of triethylamine, pyridine and carbonate.

6. The synthesis method for N-methyl-3-substituted methyl-4-pyrazolamide derivative A according to claim 2, wherein, a weight ratio of the Meldrum's acid to the first solvent to the deacid reagent is (250-270):(1000-1500):(200-240); a mole ratio of the Meldrum's acid to the compound 1 is 1:(1-1.1); a time for holding the temperature at 0° C. or below is 40-80 min; the reaction temperature is 20-25° C., and a reaction time is 18-24 h; and the pH is adjusted to 1-2 by adding the hydrochloric acid.

7. The synthesis method for N-methyl-3-substituted methyl-4-pyrazolamide derivative A according to claim 2, wherein, step S2 for synthesis of the intermediate D comprises: under the protection of nitrogen, adding the intermediate E obtained in step S1 to a second solvent, adding the compound 2, performing a heating reflux water separation reaction, performing solvent removing under a pressure to obtain a product, adding a second batch of the second solvent to the product, standing at a temperature for dissolved clarification, cooling to 0° C. or below for crystallization, filtering to obtain a filter cake, and drying to obtain the intermediate D.

8. The synthesis method for N-methyl-3-substituted methyl-4-pyrazolamide derivative A according to claim 7, wherein, in step S2, the second solvent is one selected from a group consisting of benzene, methylbenzene, chloroform and xylene, and a weight ratio of the intermediate E to the solvent is (300-400):(1000-2000), and a mole ratio of the intermediate E to the compound 2 is 1:(1-1.2); a reaction temperature of heating reflux and water separation is 80-113° C., and a reaction time of heating reflux and water separation is 4-6 h; and a weight ratio of the second solvent to the second batch of the second solvent is (2-4):1.

9. The synthesis method for N-methyl-3-substituted methyl-4-pyrazolamide derivative A according to claim 7, wherein, step S3 for synthesis of the intermediate C comprises: under the protection of nitrogen, mixing the intermediate D, an acetic anhydride and the compound 3, heating to a reaction temperature for reaction, cooling, performing reduced pressure distillation, adding ethanol, heating to realize dissolved clarification, cooling to 0° C. or below for crystallization, filtering to obtain a filter cake, and drying to obtain the intermediate C.

10. The synthesis method for N-methyl-3-substituted methyl-4-pyrazolamide derivative A according to claim 9, wherein, in step S3, a weight ratio of the intermediate D to the acetic anhydride is (450-530):(500-600), and a mole ratio of the intermediate D to the compound 3 is 1:(0.5-1); and a heating rate is 0.5-1° C./min, and an end temperature is 145° C.

11. The synthesis method for N-methyl-3-substituted methyl-4-pyrazolamide derivative A according to claim 9, wherein step S4 for synthesis of the N-methyl-3-substituted methyl-4-pyrazolamide derivative comprises: under the protection of nitrogen, adding the intermediate C obtained in step S3 to a third solvent, adding an aqueous solution of methylhydrazine dropwise, maintaining the reaction temperature for reaction, heating to a reflux temperature for further reaction, performing solvent removing under a pressure, cooling to 0° C. or below for crystallization, filtering, and drying to obtain the N-methyl-3-substituted methyl-4-pyrazolamide derivative A.

12. The synthesis method for N-methyl-3-substituted methyl-4-pyrazolamide derivative A according to claim 11, wherein, in step S4, the third solvent is one selected from a group consisting of ethanol, acetone and chloroform; a weight ratio of the intermediate C to the third solvent to the aqueous solution of methylhydrazine is (500-650):(900-1100):(130-200); the reaction temperature is 10-15° C., a time of holding the temperature for reaction is 0.5-1.5 h, a reflux temperature is 70-100° C., and a time of continuing reacting is 1-3 h.

13. A synthesis method for N-methyl-3-substituted methyl-4-pyrazolic acid B, comprising the following steps:
reacting the N-methyl-3-substituted methyl-4-pyrazolamide derivative A obtained according to claim 1 with hydrochloride acid to obtain the N-methyl-3-substituted methyl-4-pyrazolic acid B;
a structural formula of the N-methyl-3-substituted methyl-4-pyrazolic acid B is as follows:

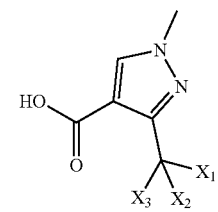

where, X1, X2 and X3 are one selected from a group consisting of H, F, Cl and Br, respectively.

14. A synthesis method for N-methyl-3-substituted methyl-4-pyrazolic acid B according to claim 13, comprising the steps of:
under protection of nitrogen, adding the N-methyl-3-substituted methyl-4-pyrazolamide derivative A and the hydrochloride acid into water, heating to a reaction temperature, refluxing for reaction, cooling to 0° C. or below, filtering, and drying to obtain the N-methyl-3-substituted methyl-4-pyrazolic acid B.

15. The synthesis method for N-methyl-3-substituted methyl-4-pyrazolic acid B according to claim 14, wherein, a weight ratio of the N-methyl-3-substituted methyl-4-pyrazolamide derivative A to the hydrochloride acid is (300-400):(150-250), a concentration of the hydrochloride acid is 20%-40%, the reaction temperature is 90-100° C., and a reaction time is 5-6 h.

* * * * *